(12) United States Patent
Yerkes et al.

(10) Patent No.: US 9,730,445 B2
(45) Date of Patent: *Aug. 15, 2017

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND FUNGICIDES

(71) Applicant: DOW AGROSCIENCES LLC, Indianapolis, IN (US)

(72) Inventors: Carla N. Yerkes, Crawfordsville, IN (US); Richard K. Mann, Franklin, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/769,606

(22) PCT Filed: Mar. 3, 2014

(86) PCT No.: PCT/US2014/019821
§ 371 (c)(1),
(2) Date: Aug. 21, 2015

(87) PCT Pub. No.: WO2014/149603
PCT Pub. Date: Sep. 25, 2014

(65) Prior Publication Data
US 2015/0373972 A1    Dec. 31, 2015

Related U.S. Application Data

(63) Continuation-in-part of application No. 13/840,236, filed on Mar. 15, 2013, now Pat. No. 8,841,234.

(51) Int. Cl.
*A01N 25/00*    (2006.01)
*A01N 43/54*    (2006.01)
(Continued)

(52) U.S. Cl.
CPC .................. *A01N 43/40* (2013.01)

(58) Field of Classification Search
None
See application file for complete search history.

(56) References Cited

U.S. PATENT DOCUMENTS 7,314,849 B2    1/2008 Balko et al.
7,622,641 B2    11/2009 McCutchen et al.
(Continued)

FOREIGN PATENT DOCUMENTS

WO    2007082098    7/2007
WO    2009029518    3/2009
(Continued)

OTHER PUBLICATIONS

International Searching Authority, International Search Report and Written Opinion for PCT/US2014/019821, dated Jun. 3, 2014, 9 pages.
(Continued)

*Primary Examiner* — Alton Pryor
(74) *Attorney, Agent, or Firm* — Michael R. Asam; Faegre Baker Daniels LLP

(57) ABSTRACT

Provided herein are synergistic herbicidal compositions containing (a) a compound of formula (I): or an agriculturally acceptable salt or ester thereof and (b) fungicides, including but not limited to, azoxystrobin, carbendazim, difenoconazole, flutolanil, hexaconazole, iprobenfos, isoprothiolane, isotianil, kasugamycin, mancozeb, myclobutanil, phthalide, probenazole, propiconazole, pyroquilon, tebuconazole, thifluzamide, tricyclazole, trifloxystrobin, validamycin, or a compound of formula (II) The compositions and methods provided herein control undesirable vegetation, e.g., in direct-seeded, water-seeded and transplanted rice, cereals, wheat, barley, oats, rye, *sorghum*, corn/maize, sugarcane, sunflower, oilseed rape, canola, sugar beet, soybean, cotton, pineapple, pastures, grasslands, rangelands, fallowland, turf, tree and vine orchards, plantation crops, vegetables, industrial vegetation management (IVM) and rights-of-way (ROW).

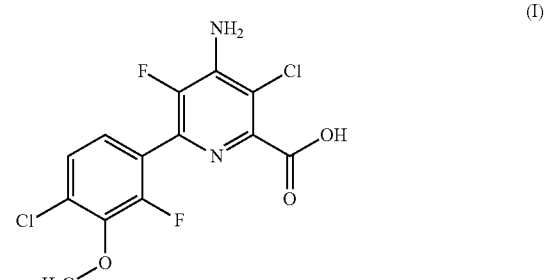

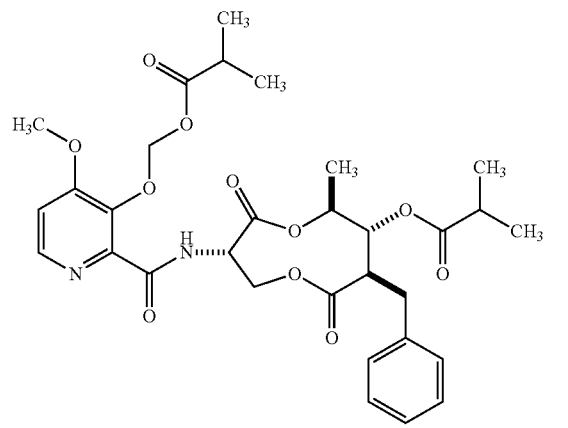

21 Claims, No Drawings

(51) Int. Cl.
| | |
|---|---|
| *A01N 43/66* | (2006.01) |
| *A01N 43/40* | (2006.01) |
| *A01N 43/42* | (2006.01) |
| *A01N 43/64* | (2006.01) |
| *A01N 43/653* | (2006.01) |
| *A01N 43/707* | (2006.01) |

(56) References Cited

U.S. PATENT DOCUMENTS

| | | | |
|---|---|---|---|
| 8,791,048 | B2 | 7/2014 | Yerkes et al. |
| 8,796,177 | B2 | 8/2014 | Mann et al. |
| 8,809,232 | B2 | 8/2014 | Yerkes et al. |
| 8,841,233 | B2 | 9/2014 | Yerkes et al. |
| 8,841,234 | B1 * | 9/2014 | Mann .................... A01N 43/40 504/100 |
| 8,846,570 | B2 | 9/2014 | Yerkes et al. |
| 8,871,680 | B2 | 10/2014 | Yerkes et al. |
| 8,871,681 | B2 | 10/2014 | Mann et al. |
| 8,883,682 | B2 | 11/2014 | Yerkes et al. |
| 8,889,591 | B2 | 11/2014 | Yerkes et al. |
| 8,895,470 | B2 | 11/2014 | Yerkes et al. |
| 8,901,035 | B2 | 12/2014 | Yerkes et al. |
| 8,906,825 | B2 | 12/2014 | Mann et al. |
| 8,906,826 | B2 | 12/2014 | Yerkes et al. |
| 8,912,120 | B2 | 12/2014 | Yerkes et al. |
| 8,912,121 | B2 | 12/2014 | Yerkes et al. |
| 8,916,499 | B2 | 12/2014 | Yerkes et al. |
| 9,119,397 | B2 | 9/2015 | Yerkes et al. |
| 2009/0062121 | A1 | 3/2009 | Satchivi et al. |
| 2010/0137137 | A1 | 6/2010 | Rosinger et al. |
| 2011/0082162 | A1 | 4/2011 | Lorsbach et al. |
| 2011/0207607 | A1 | 8/2011 | Satchivi et al. |
| 2012/0088667 | A1 | 4/2012 | Williams et al. |
| 2012/0115727 | A1 | 5/2012 | Satchivi et al. |
| 2012/0190551 | A1 | 7/2012 | Yerkes et al. |
| 2013/0109569 | A1 | 5/2013 | Dave et al. |
| 2013/0310256 | A1 | 11/2013 | Yerkes et al. |
| 2015/0018208 | A1 | 1/2015 | Yerkes et al. |
| 2015/0189879 | A1 | 7/2015 | Mann et al. |

FOREIGN PATENT DOCUMENTS

| | | |
|---|---|---|
| WO | 2010116264 A2 | 10/2010 |
| WO | 2011103240 A1 | 8/2011 |

OTHER PUBLICATIONS

Synthesis of Esters: Esterification Reactions, obtained via google.com in U.S. Appl. No. 13/840,306, obtained online Mar. 8, 2014, 1 page.
Steglich Esterification, Organic Chemistry Portal in U.S. Appl. No. 13/840,306, obtained online Mar. 9, 2014, 2 pages.
Chui, M.P., USPTO, Final Office Action in U.S. Appl. No. 13/840,306, dated Sep. 25, 2014, 13 pages.
Chui, M.P., USPTO, Non-Final Office Action in U.S. Appl. No. 13/840,306, dated Mar. 13, 2014, 12 pages.
Pryor, A.N., USPTO, Non-Final Office Action for U.S. Appl. No. 13/840,488, dated Dec. 31, 2013, 6 pages.
Pryor, A.N., USPTO, Non-Final Office Action for U.S. Appl. No. 13/840,346, dated Jan. 1, 2014, 5 pages.
Pryor, A.N., USPTO, Non-Final Office Action for U.S. Appl. No. 13/840,303, dated Jan. 3, 2014, 5 pages.
Pryor, A.N., USPTO, Non-Final Office Action for U.S. Appl. No. 13/833,372, dated Jan. 2, 2014, 5 pages.
Pryor, A.N., USPTO Non-Final Office Action for U.S. Appl. No. 13/836,653, dated Nov. 7, 2013, 7 pages.
Pryor, A.N., USPTO, Non-Final Office Action for U.S. Appl. No. 13/839,043, dated Nov. 6, 2013, 7 pages.
Pryor, A.N., USPTO, Non-Final Office Action for U.S. Appl. No. 13/837,990, dated Nov. 6, 2013, 7 pages.
Pryor, A.N., USPTO, Non-Final Office Action for U.S. Appl. No. 13/840,236, dated Jan. 3, 2014, 6 pages.
Pryor, A.N., USPTO, Non-Final Office Action for U.S. Appl. No. 13/840,419, dated Dec. 31, 2013, 5 pages.
Pryor, A.N., USPTO, Notice of Allowance and Fee(s) Due for U.S. Appl. No. 13/832,978, dated Apr. 9, 2014, 13 pages.
Pryor, A.N., USPTO, Supplemental/Correct Notice of Allowability for U.S. Appl. No. 13/833,315, dated May 12, 2014, 19 pages.
Pryor, A.N., USPTO, Notice of Allowance and Fee(s) Due for U.S. Appl. No. 13/833,362, dated May 29, 2014, 8 pages.
Pryor, A.N., USPTO, Notice of Allowance and Fee(s) Due for U.S. Appl. No. 13/833,372, dated May 14, 2014, 8 pages.
Pryor, A.N., USPTO, Notice of Allowance and Fee(s) Due for U.S. Appl. No. 13/833,659, dated Mar. 17, 2014, 12 pages.
Pryor, A.N., USPTO, Notice of Allowance and Fee(s) Due for U.S. Appl. No. 13/833,923, dated May 2, 2014, 9 pages.
Pryor, A.N., USPTO, Notice of Allowance and Fee(s) Due for U.S. Appl. No. 13/833,965, dated Apr. 1, 2014, 8 pages.
Pryor, A.N., USPTO, Notice of Allowance and Fee(s) Due for U.S. Appl. No. 13/834,706, dated Mar. 12, 2014, 13 pages.
Pryor, A.N., USPTO, Notice of Allowance and Fee(s) Due for U.S. Appl. No. 13/837,990, dated Apr. 1, 2014, 8 pages.
Pryor, A.N., USPTO, Supplemental/Correct Notice of Allowability for U.S. Appl. No. 13/839,043, dated May 27, 2014, 13 pages.
Pryor, A.N., USPTO, Notice of Allowance and Fee(s) Due for U.S. Appl. No. 13/840,236, dated Apr. 25, 2014, 8 pages.
Pryor, A.N., USPTO, Notice of Allowance and Fee(s) Due for U.S. Appl. No. 13/840,303, dated Apr. 25, 2014, 8 pages.
Pryor, A.N., USPTO, Notice of Allowance and Fee(s) Due for U.S. Appl. No. 13/840,419, dated May 5, 2014, 8 pages.
Pryor, A.N., USPTO, Notice of Allowance and Fee(s) Due for U.S. Appl. No. 13/840,488, dated May 2, 2014, 8 pages.
Pryor, A.N., USPTO, Supplemental/Correct Notice of Allowability for U.S. Appl. No. 13/834,326, dated May 13, 2014, 13 pages.
Pryor, A.N., USPTO, Notice of Allowance and Fee(s) Due for U.S. Appl. No. 13/836,653, dated Apr. 2, 2014, 8 pages.
Pryor, A.N., USPTO, Notice of Allowance and Fee(s) Due for U.S. Appl. No. 13/840,346, dated Jun. 4, 2014, 8 pages.
Pryor, A.N., USPTO, Non-Final Office Action for U.S. Appl. No. 14/502,591, dated Dec. 19, 2014, 5 pages.
Pryor, A.N., USPTO, Notice of Allowance and Fee(s) Due for U.S. Appl. No. 14/502,591, dated Apr. 23, 2015, 9 pages.

* cited by examiner

HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND FUNGICIDES

CROSS-REFERENCE TO RELATED APPLICATIONS

This application is a U.S. National Phase Patent Application based on International Application No. PCT/US2014/019821 filed Mar. 3, 2014, which is a continuation-in-part of U.S. application Ser. No. 13/840,236, filed Mar. 15, 2013, now U.S. Pat. No. 8,841,234, the entire disclosures of which are hereby expressly incorporated herein by reference.

FIELD

Provided herein are compositions comprising (a) 4-amino-3-chloro-5-fluoro-6-(4-chloro-2-fluoro-3-methoxyphenyl) pyridine-2-carboxylic acid or an agriculturally acceptable ester or salt thereof and (b) fungicides. Provided herein are also methods of controlling undesirable vegetation comprising applying (a) 4-amino-3-chloro-5-fluoro-6-(4-chloro-2-fluoro-3-methoxyphenyl)pyridine-2-carboxylic acid or an agriculturally acceptable ester or salt thereof and (b) fungicides.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

A first embodiment including a herbicidal composition comprising a herbicidally effective amount of (a) a compound of the formula (I)

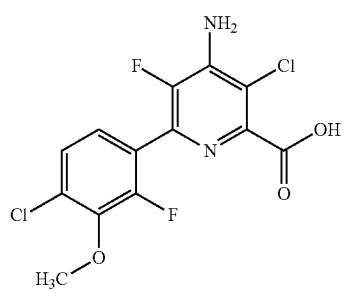

(I)

or an agriculturally acceptable salt or ester thereof and a compound selected from the group consisting of: (b) azoxystrobin, carbendazim, difenoconazole, flutolanil, hexaconazole, iprobenfos, isoprothiolane, isotianil, kasugamycin, mancozeb, myclobutanil, phthalide, probenazole, propiconazole, pyroquilon, tebuconazole, thifluzamide, tricyclazole, trifloxystrobin, validamycin, and a compound of formula (II)

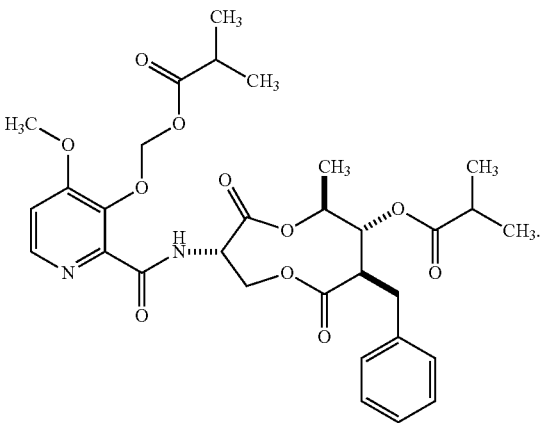

(II)

A second embodiment, including the composition according to the first embodiment, wherein (a) is a $C_1$-$C_4$ alkyl or benzyl ester of compound (I).

A third embodiment, including the composition according to the first embodiment, wherein (a) is a $C_1$-$C_4$ alkyl ester of compound (I).

A fourth embodiment including the composition according to the second embodiment, wherein (a) is a benzyl ester of compound (I).

A fifth embodiment including the composition according to the first embodiment, wherein (a) is the compound of formula (I), which is the carboxylic acid.

A sixth embodiment including the compositions according to the first through the fifth embodiments, further comprising at least one compound selected from the group consisting of: a herbicide safener, carrier and adjuvant.

A seventh embodiment including at least one composition according to any of the first through the sixth embodiments, wherein the ratios of the compound of formula (I) or agriculturally acceptable salt or ester thereof to azoxystrobin in units of grams (g) to g, grams acid equivalent per hectare (g ae/ha) to g ae/ha, or g ae/ha to grams active ingredient per hectare (g ai/ha) is from about 1:500 to about 12:1.

An eighth embodiment including at least one composition according to any of the first through the sixth embodiments wherein the ratios of the compound of formula (I) or agriculturally acceptable salt or ester thereof to carbendazim in units of g to g, g ae/ha to g ae/ha, or g ae/ha to g ai/ha is from about 1:375 to about 12:1.

A ninth embodiment including at least one composition according to any of the first through the sixth embodiments wherein the ratios of the compound of formula (I) or agriculturally acceptable salt or ester thereof to difenoconazole in units of g to g, g ae/ha to g ae/ha, or g ae/ha to g ai/ha is from about 1:250 to about 12:1.

A tenth embodiment including at least one composition according to any of the first through the sixth embodiments wherein the ratios of the compound of formula (I) or agriculturally acceptable salt or ester thereof to flutolanil in units of g to g, g ae/ha to g ae/ha, or g ae/ha to g ai/ha is from about 1:500 to about 12:1.

An eleventh embodiment including at least one composition according to any of the first through the sixth embodiments wherein the ratios of the compound of formula (I) or agriculturally acceptable salt or ester thereof to hexaconazole in units of g to g, g ae/ha to g ae/ha, or g ae/ha to g ai/ha is from about 1:250 to about 60:1.

A twelfth embodiment including at least one composition according to any of the first through the sixth embodiments wherein the ratios of the compound of formula (I) or agriculturally acceptable salt or ester thereof to iprobenfos in units of g to g, g ae/ha to g ae/ha, or g ae/ha to g ai/ha is from about 1:1000 to about 3:1.

A thirteenth embodiment including at least one composition according to any of the first through the sixth embodiments wherein the ratios of the compound of formula (I) or agriculturally acceptable salt or ester thereof to isoprothiolane in units of g to g, g ae/ha to g ae/ha, or g ae/ha to g ai/ha is from about 1:500 to about 6:1.

A fourteenth embodiment including at least one composition according to any of the first through the sixth embodiments wherein the ratios of the compound of formula (I) or agriculturally acceptable salt or ester thereof to isotianil in units of g to g, g ae/ha to g ae/ha, or g ae/ha to g ai/ha is from about 1:500 to about 30:1.

A fifteenth embodiment including at least one composition according to any of the first through the sixth embodiments wherein the ratios of the compound of formula (I) or agriculturally acceptable salt or ester thereof to kasugamycin in units of g to g, g ae/ha to g ae/ha, or g ae/ha to g ai/ha is from about 1:250 to about 150:1.

A sixteenth embodiment including at least one composition according to any of the first through the sixth embodiments wherein the ratios of the compound of formula (I) or agriculturally acceptable salt or ester thereof to mancozeb in units of g to g, g ae/ha to g ae/ha, or g ae/ha to g ai/ha is from about 1:2500 to about 12:1.

A seventeenth embodiment including at least one composition according to any of the first through the sixth embodiments wherein the ratios of the compound of formula (I) or agriculturally acceptable salt or ester thereof to myclobutanil in units of g to g, g ae/ha to g ae/ha, or g ae/ha to g ai/ha is from about 1:250 to about 12:1.

An eighteenth embodiment including at least one composition according to any of the first through the sixth embodiments wherein the ratios of the compound of formula (I) or agriculturally acceptable salt or ester thereof to phthalide in units of g to g, gae/ha to gae/ha, or gae/ha gai/ha is from about 1:500 to about 15:1.

A nineteenth embodiment including at least one composition according to any of the first through the sixth embodiments wherein the ratios of the compound of formula (I) or agriculturally acceptable salt or ester thereof to probenazole in units of g to g, g ae/ha to g ae/ha, or g ae/ha to gai/ha is from about 1:2500 to about 6:1.

A twentieth embodiment including at least one composition according to any of the first through the sixth embodiments wherein the ratios of the compound of formula (I) or agriculturally acceptable salt or ester thereof to propiconazole in units of g to g, g ae/ha to g ae/ha, or g ae/ha to g ai/ha is from about 1:250 to about 30:1.

A twenty-first embodiment including at least one composition according to any of the first through the sixth embodiments wherein the ratios of the compound of formula (I) or agriculturally acceptable salt or ester thereof to pyroquilon in units of g to g, g ae/ha to g ae/ha, or g ae/ha to g ai/ha is from about 1:1500 to about 3:1.

A twenty-second embodiment including at least one composition according to any of the first through the sixth embodiments wherein the ratios of the compound of formula (I) or agriculturally acceptable salt or ester thereof to tebuconazole in units of g to g, g ae/ha to g ae/ha, or g ae/ha to g ai/ha is from about 1:250 to about 12:1.

A twenty-third embodiment including at least one composition according to any of the first through the sixth embodiments wherein the ratios of the compound of formula (I) or agriculturally acceptable salt or ester thereof to thifluzamide in units of g to g, g ae/ha to g ae/ha, or g ae/ha to g ai/ha is from about 1:375 to about 30:1.

A twenty-fourth embodiment including at least one composition according to any of the first through the sixth embodiments wherein the ratios of the compound of formula (I) or agriculturally acceptable salt or ester thereof to tricyclazole in units of g to g, g ae/ha to g ae/ha, or g ae/ha to g ai/ha is from about 1:500 to about 15:1.

A twenty-fifth embodiment including at least one composition according to any of the first through the sixth embodiments wherein the ratios of the compound of formula (I) or agriculturally acceptable salt or ester thereof to trifloxystrobin in units of g to g, g ae/ha to g ae/ha, or g ae/ha to g ai/ha is from about 1:250 to about 30:1.

A twenty-sixth embodiment including at least one composition according to any of the first through the sixth embodiments wherein the ratios of the compound of formula (I) or agriculturally acceptable salt or ester thereof to validamycin in units of g to g, g ae/ha to g ae/ha, or g ae/ha to g ai/ha is from about 1:25 to about 3000:1.

A twenty-seventh embodiment including at least one composition according to any of the first through the sixth embodiments wherein the ratios of the compound of formula (I) or agriculturally acceptable salt or ester thereof to a compound of formula (II) in units of g to g, g ae/ha to g ae/ha, or g ae/ha to g ai/ha is from about 1:375 to about 150:1.

A twenty-eighth embodiment includes methods for controlling undesirable vegetation which comprises contacting the vegetation or the area adjacent to the vegetation with or applying to the soil or water to prevent the emergence or growth of vegetation the composition of any of the compositions according to the first through the twenty-seventh embodiments.

A twenty-ninth embodiment includes methods of controlling undesirable vegetation which comprises contacting the vegetation or the area adjacent to the vegetation with or applying to the soil or water to prevent the emergence or growth of vegetation a herbicidally effective amount of (a) a compound of the formula (I)

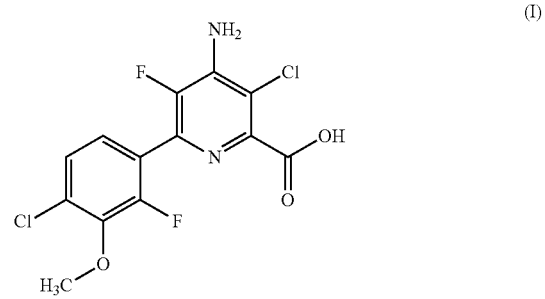 [SMILES: COc1c(Cl)ccc(-c2nc(C(=O)O)c(Cl)c(N)c2F)c1F]

or an agriculturally acceptable salt or ester thereof and a compound selected from the group consisting of: (b) azoxystrobin, carbendazim, difenoconazole, flutolanil, hexaconazole, iprobenfos, isoprothiolane, isotianil, kasugamycin, mancozeb, myclobutanil, phthalide, probenazole, propiconazole, pyroquilon, tebuconazole, thifluzamide, tricyclazole, trifloxystrobin, validamycin, and a compound of formula (II)

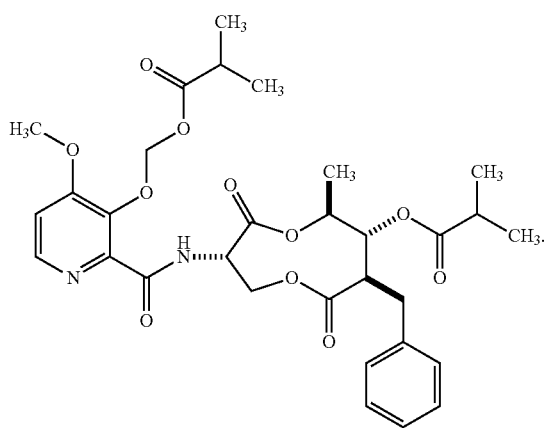

A thirtieth embodiment includes methods according to any of the twenty-eighth and twenty-ninth embodiments for controlling undesired vegetation, wherein the undesirable vegetation is controlled in direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, plantation crops, vegetables, industrial vegetation management (IVM) and rights-of-way (ROW).

A thirty-first embodiment includes methods according to any of the twenty-eighth and twenty-ninth embodiments, wherein the undesirable vegetation is immature.

A thirty-second embodiment includes methods according to any of the twenty-eighth and twenty-ninth embodiments, wherein the compounds (a) and (b) are applied to water.

The thirty-third embodiment includes methods according to the thirty-second embodiment wherein the water is part of a flooded rice paddy.

A thirty-fourth embodiment includes methods according to any of the twenty-eighth and twenty-ninth embodiments wherein the compound (a) and (b) are applied pre-emergently and/or post emergently to the weed or the crop.

A thirty-fifth embodiment includes methods according to any of the twenty-eighth and twenty-ninth embodiments, wherein the undesirable vegetation is controlled in glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant crops.

A thirty-sixth embodiment includes methods according to the thirty-fifth embodiment, wherein the tolerant crop possesses multiple or stacked traits conferring tolerance to multiple herbicides or multiple modes-of-action.

A thirty-seventh embodiment includes methods according to the twenty-eighth and twenty-ninth embodiments, wherein the undesirable vegetation comprises a herbicide resistant or tolerant weed.

A thirty-eighth embodiment includes methods according to the thirty-seventh embodiment, wherein the resistant or tolerant weed is a biotype with resistance or tolerance to multiple herbicides, multiple chemical classes, multiple herbicide modes-of-action, or via multiple resistance mechanisms.

The thirty-ninth embodiment includes methods according to any of the thirty-seventh and thirty ninth embodiments, wherein the resistant or tolerant weed is a biotype resistant or tolerant to acetolactate synthase (ALS) or acetohydroxy acid synthase (AHAS) inhibitors, photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

Provided herein are herbicidal compositions comprising a herbicidally effective amount of (a) a compound of the formula (I)

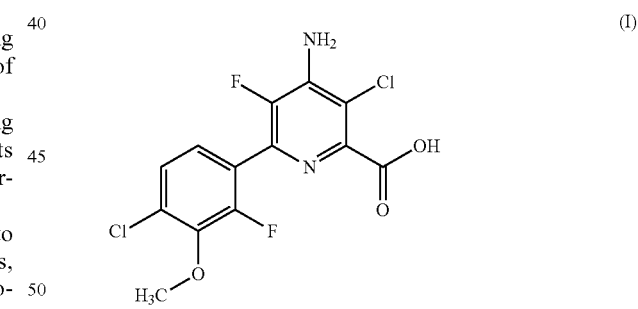

or an agriculturally acceptable salt or ester of thereof, and (b) fungicides. The compositions may also contain an agriculturally acceptable adjuvant or carrier. Provided herein are also methods of controlling undesirable vegetation comprising applying (a) a compound of formula (I) or an agriculturally acceptable ester or salt thereof and (b) fungicides.

DETAILED DESCRIPTION

Definitions

As used herein, the compound of formula (I) has the following structure:

(I)

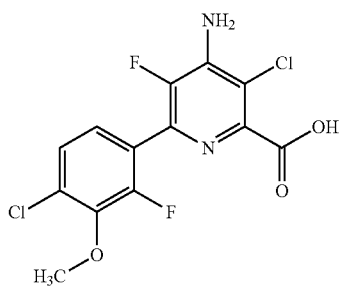

The compound of formula (I) can be identified by the name 4-amino-3-chloro-6-(4-chloro-2-fluoro-3-methoxyphenyl)-5-fluoropyridine-2-carboxylic acid or 4-amino-3-chloro-5-fluoro-6-(4-chloro-2-fluoro-3-methoxyphenyl)pyrimidine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

Fungicides are a class of pesticides used to control plant pathogens in crop and non-crop settings. Without being limited to any theory, these pesticides kill diseases/plant pathogens via multiple, different modes-of-action. Exemplary uses of fungicides include their use to control plant diseases and plant pathogens in cereal, legume, vegetable, fruit, row and perennial crops.

Exemplary fungicides include, but are not limited to, azoxystrobin, carbendazim, difenoconazole, flutolanil, hexaconazole, iprobenfos, isoprothiolane, isotianil, kasugamycin, mancozeb, myclobutanil, phthalide, probenazole, propiconazole, pyroquilon, tebuconazole, thifluzamide, tricyclazole, trifloxystrobin, validamycin, and a compound of formula (II):

(II)

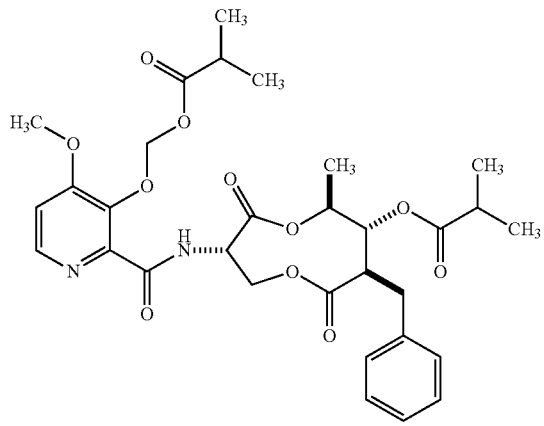

As used herein, azoxystrobin is methyl (2E)-2-{2-[6-(2-cyanophenoxy)pyrimidin-4-yloxy]phenyl}3-methoxyacrylate and possesses the following structure:

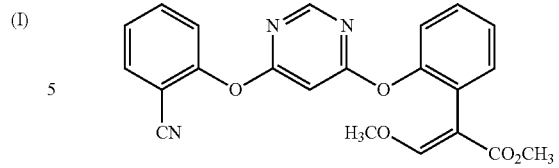

Its fungicidal activity is exemplified in Tomlin, C. D. S., Ed. *The Pesticide Manual: A World Compendium,* 15th ed.; BCPC Publications: Alton, 2009 (hereafter "*The Pesticide Manual*, Fifteenth Edition, 2009"). Exemplary uses of azoxystrobin include its use as a protectant, curative and eradicant fungicide for the control of many plant pathogens in crops, including *Pyricularia* and *Rhizoctonia* in rice. Azoxystrobin can be applied, e.g., as a post-emergence treatment to control undesirable plant pathogens.

As used herein, carbendazim is methyl benzimidazol-2-ylcarbamate and possesses the following structure:

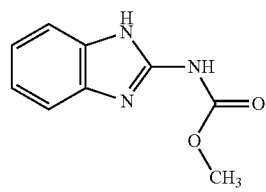

Its fungicidal activity is exemplified in *The Pesticide Manual*, Fifteenth Edition, 2009. Exemplary uses of carbendazim include its use as a systemic fungicide with protective and curative action for the control of *Septoria, Fusarium, Erysiphe* and other diseases in cereal crops. Carbendazim can be applied, e.g., post-emergence to control undesirable plant pathogens.

As used herein difenoconazole is cis, trans-3-chloro-4-[4-methyl-2-(1H-1,2,4-triazol-1-ylmethyl)-1,3,dioxolan-2-yl]phenyl 4-chlorophenyl ether and possesses the following structure:

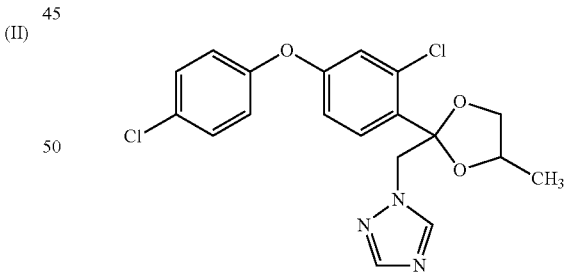

Its fungicidal activity is exemplified in *The Pesticide Manual*, Fifteenth Edition, 2009. Exemplary uses of difenoconazole include its use as a systemic fungicide with preventative and curative activity for the control of plant diseases in many crops, including *Rhizoctonia, Cercospora, Septoria* and many other diseases in rice, cereals, oilseed rape, etc. Difenoconazole can be applied, e.g., as a post-emergence treatment to control undesirable plant pathogens.

As used herein, flutolanil is α,α,α-trifluoro-3'-isopropoxy-o-toluanilide and possesses the following structure:

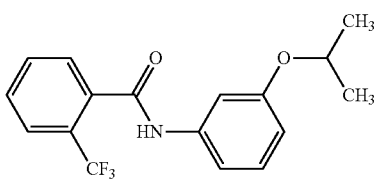 [SMILES: CC(C)Oc1cccc(NC(=O)c2ccccc2C(F)(F)F)c1]

Its fungicidal activity is exemplified in *The Pesticide Manual*, Fifteenth Edition, 2009. Exemplary uses of flutolanil include its use as a systemic fungicide for the control of *Rhizoctonia* in many crops, including rice, cereals, turf, etc. Flutolanil can be applied, e.g., as a post-emergence treatment to control undesirable plant pathogens.

As used herein, hexaconazole is (RS)-2-(2,4-dichlorophenyl)-1-(1H-1,2,4-triazol-1-yl)hexan-2-ol) and possesses the following structure:

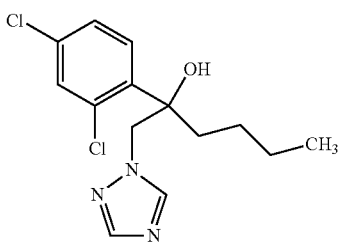 [SMILES: CCCCC(O)(Cn1cncn1)c1ccc(Cl)cc1Cl]

Its fungicidal activity is exemplified in *The Pesticide Manual*, Fifteenth Edition, 2009. Exemplary uses of hexaconazole include its use for the control of Ascomycetes and Basidiomycetes in vine, coffee, and other crops. Hexaconazole can be applied, e.g., as a post-emergence treatment to control undesirable plant pathogens.

As used herein, iprobenfos is S-benzyl O,O-diisopropyl phosphorothioate and possesses the following structure:

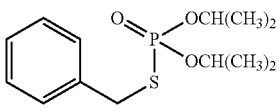

Its fungicidal activity is exemplified in *The Pesticide Manual*, Fifteenth Edition, 2009. Exemplary uses of iprobenfos include its use as a systemic fungicide for the control of rice blast (*Pyricularia*), stem rot and sheath blight (*Rhizoctonia*) in rice. Iprobenfos can be applied, e.g., as a post-emergence treatment to control undesirable plant pathogens.

As used herein, isoprothiolane is diisopropyl 1,3-dithiolan-2-ylidenemalonate and possesses the following structure:

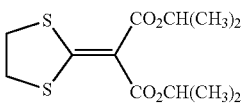

Its fungicidal activity is exemplified in *The Pesticide Manual*, Fifteenth Edition, 2009. Exemplary uses of isoprothiolane include its use as a systemic fungicide that inhibits penetration and elongation of infection hyphae for the control of *Pyricularia* and other diseases in rice and other crops. Isoprothiolane can be applied, e.g., post-emergence treatment to control undesirable plant pathogens.

As used herein isotianil is 3,4-dichloro-2'-cyano-1,2-thiazole-5-carboxanilide and possesses the following structure:

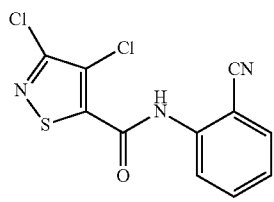 [SMILES: N#Cc1ccccc1NC(=O)c1snc(Cl)c1Cl]

Its fungicidal activity is exemplified in *The Pesticide Manual*, Fifteenth Edition, 2009 and/or *The Pesticide Manual* 2011 electronic edition. Exemplary uses of isotianil include its use for the control of rice blast (*Pyricularia*) in rice. Isotianil can be applied, e.g., post-emergence or rice nursery box drench treatment to control undesirable plant pathogens.

As used herein, kasugamycin as the hydrochloride hydrate is 1L-1,3,4/2,5,6-1-deoxy-2,3,4,5,6,-pentahydroxycyclohexyl 2-amino-2,3,4,6-tetradeoxy-4-(α-iminoglycino)-α-D-arabino-hexopyranoside hydrochloride hydrate and possesses the following structure:

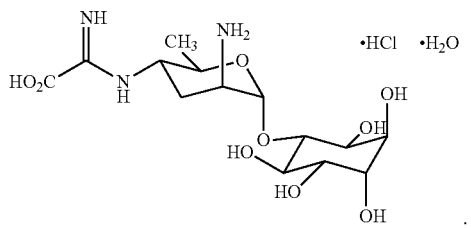 [SMILES: CC1OC(OC2C(O)C(O)C(O)C(O)C2O)C(N)CC1NC(=N)C(=O)O ; Cl ; O]

Its fungicidal activity is exemplified in *The Pesticide Manual*, Fifteenth Edition, 2009. Exemplary uses of kasugamycin include its use as a systemic fungicide and bactericide that inhibits hyphal growth of rice blast (*Pyricularia*) in rice. Kasugamycin can be applied, e.g., as a rice nursery drench and post-emergence treatments to control undesirable plant pathogens.

As used herein, mancozeb is manganese ethylenebis(dithiocarbamate) (polymeric) complex with zinc salt and possesses the following structure:

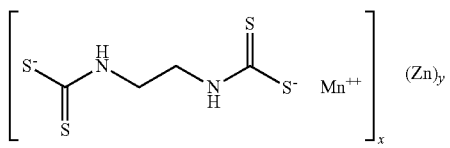

x:y = 1:0.091

Its fungicidal activity is exemplified in *The Pesticide Manual*, Fifteenth Edition, 2009. Exemplary uses of mancozeb include its use as a protectant fungicide for the control of many fungal diseases in many crops. Mancozeb is a fungal respiration inhibitor, and can be applied, e.g., as post-emergence and as a seed treatment to control many undesirable plant pathogens.

As used herein, myclobutanil is 2-p-chlorophenyl-2-(1H-1,2,4-triazol-1-ylmethyl)hexanenitrile and possesses the following structure:

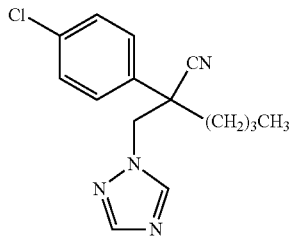

Its fungicidal activity is exemplified in *The Pesticide Manual*, Fifteenth Edition, 2009. Exemplary uses of myclobutanil, a known ergosterol biosynthesis inhibitor with protective and curative properties, include its use for the control of Ascomycetes, Fungi Imperfecti and Basidomycetes in many crops. Myclobutanil can be applied, e.g., post-emergence and as a seed treatment to control undesirable plant pathogens.

As used herein, phthalide is 4,5,6,7-tetrachlorophthalide and possesses the following structure:

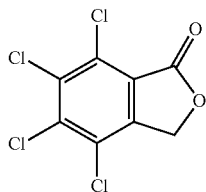 [SMILES: O=C1OCc2c(Cl)c(Cl)c(Cl)c(Cl)c21]

Its fungicidal activity is exemplified in *The Pesticide Manual*, Fifteenth Edition, 2009. Exemplary uses of phthalide include its use for the control of rice blast (*Pyricularia oryzae*) in rice. Phthalide can be applied, e.g., as a drench and post-emergence to control rice blast in rice.

As used herein, probenazole, is 3-allyloxy-1,2-benz[d]isothiazole 1,1-dioxide and possesses the following structure:

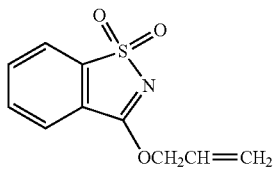

Its fungicidal activity is exemplified in *The Pesticide Manual*, Fifteenth Edition, 2009. Exemplary uses of probenazole include its use for the control of rice blast and leaf blight in transplanted rice. Probenazole can be applied, e.g., as a post-emergence treatment to control undesirable plant pathogens in rice.

As used herein, propiconazole is 1-[2-(2,4-dichlorophenyl)-4-propyl-1,3-dioxolan-2-ylmethyl]-1H-1,2,4-triazole and possesses the following structure:

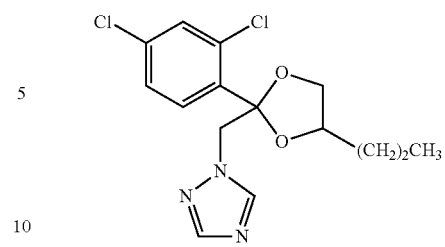

Its fungicidal activity is exemplified in *The Pesticide Manual*, Fifteenth Edition, 2009. Exemplary uses of propiconazole include its use for the control of *Rhizoctonia* and dirty panicle complex in rice, as well as many diseases in cereal, turf and corn crops. Propiconazole can be applied, e.g., as a post-emergence treatment to control undesirable plant pathogens in many crops.

As used herein, pyroquilon is 1,2,5,6-tetrahydropyrrolo[3,2,1-ij]quinolin-4-one and possesses the following structure:

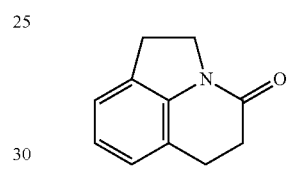

Its fungicidal activity is exemplified in *The Pesticide Manual*, Fifteenth Edition, 2009. Exemplary uses of pyroquilon, a known melanin biosynthesis inhibitor, include its use for the control of *Pyricularia* in rice. Pyroquilon can be applied, e.g., as a post-emergence and seed drench treatment to control undesirable plant pathogens in rice.

As used herein, tebuconazole is (RS)-1-p-chlorophenyl-4,4-dimethyl-3-(1H-1,2,4-triazol-1-ylmethyl)pentan-3-ol and possesses the following structure:

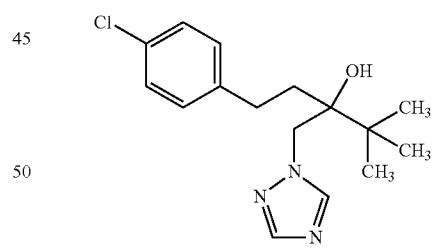

Its fungicidal activity is exemplified in *The Pesticide Manual*, Fifteenth Edition, 2009. Tebuconazole acts by inhibition of ergosterol biosynthesis, providing protective, curative and eradicant activity. Exemplary uses of tebuconazole include its use for the control of many diseases across many crops, including *Puccinia, Fusarium, Erysiphe* and other diseases. Tebuconazole can be applied, e.g., as a post-emergence treatment to control undesirable plant pathogens.

As used herein, thifluzamide is 2',6'-dibromo-2-methyl-4'-trifluoromethoxy-4-trifluoromethyl-1,3-thiazole-5-carboxanilide and possesses the following structure:

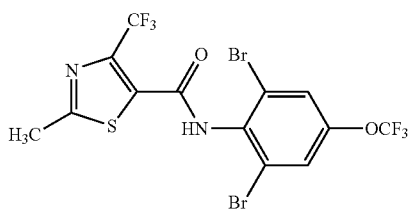 [SMILES: Cc1nc(C(F)(F)F)c(C(=O)Nc2c(Br)cc(OC(F)(F)F)cc2Br)s1]

Its fungicidal activity is exemplified in *The Pesticide Manual*, Fifteenth Edition, 2009. Exemplary uses of thifluzamide include its use for the control of Basidiomycetes, including diseases caused by *Rhizoctonia* spp. in rice and cereal crops. Thifluzamide can be applied, e.g., as post-emergence and as a seed treatment to control undesirable plant pathogens.

As used herein, tricyclazole is 5-methyl-1,2,4-triazolo[3,4-b][1,3]benzothiazole and possesses the following structure:

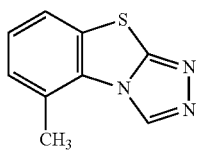

Its fungicidal activity is exemplified in *The Pesticide Manual*, Fifteenth Edition, 2009. Exemplary uses of tricyclazole, a known melanin biosynthesis inhibitor, include its use for the control of rice blast (*Pyricularia oryzae*) in seeded and transplanted rice. Tricyclazole can be applied, e.g., as a post-emergence, seed or soak treatment to control undesirable plant pathogens in rice.

As used herein, trifloxystrobin is methyl (E)-methoxy-imino-{(E)-α-[1-(α,α,α-trifluoro-m-tolyl)ethylideneaminooxy]-o-tolyl}acetate and possesses the following structure:

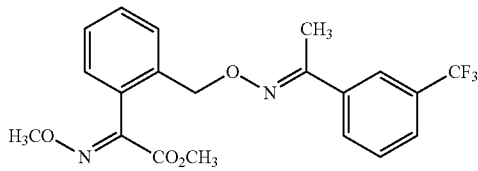 [SMILES: CO/N=C(/C(=O)OC)c1ccccc1CO/N=C(\C)c1cccc(C(F)(F)F)c1]

Its fungicidal activity is exemplified in *The Pesticide Manual*, Fifteenth Edition, 2009. Exemplary uses of trifloxystrobin include its use for the control of rusts and powdery mildew in cereal, fruit and vegetable crops. Trifloxystrobin can be applied, e.g., as a post-emergence treatment to control undesirable plant pathogens.

As used herein, validamycin is 1L-(1R,2R,3S,4S,6R)-2,3-dihydroxy-6-(hydroxymethyl)-4-{[(1S,4S,5S,6S)-4,5,6-trihydroxy-3-(hydroxymethyl)cyclohex-2-en-1-yl]amino}cyclohexyl β-D-glucopyranoside and possesses the following structure:

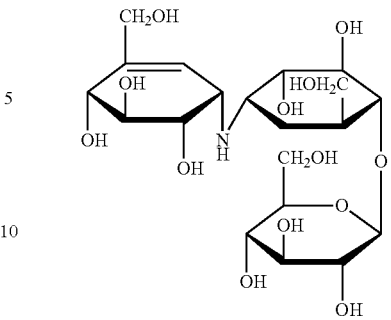

Its fungicidal activity is exemplified in *The Pesticide Manual*, Fifteenth Edition, 2009. Exemplary uses of validamycin include its use for the control of *Rhizoctonia solani* in rice and many other crops. Validamycin can be applied, e.g., post-mergence, as a soil drench or seed treatment to control undesirable plant pathogens.

As used herein, a compound of formula (II) possesses the following structure:

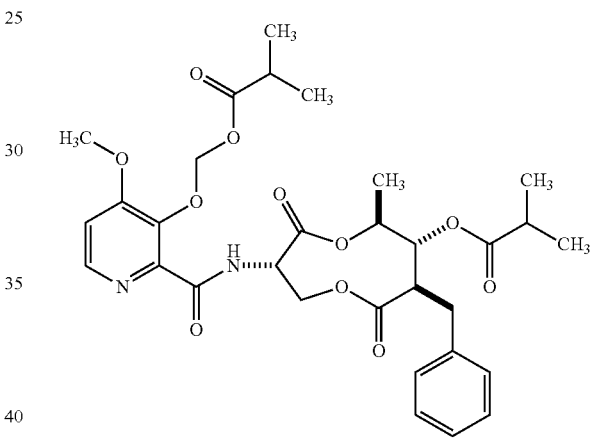

Its fungicidal activity is exemplified in: International Patent Publication No. WO 03/035617, published May 1, 2003. Exemplary uses of a compound of formula (II) include its use for the control of rust and other diseases in cereal crops. A compound of formula (II) can be applied, e.g., as a post-emergence treatment to control undesirable plant pathogens.

As used herein, fungicide means a compound, e.g., active ingredient that kills, controls or otherwise adversely modifies the growth of plant diseases/pathogens. As used herein, fungicide means a compound, e.g., active ingredient that kills, controls or otherwise adversely modifies the growth of fungi.

As used herein, a fungicidally effective or controlling amount is an amount of active ingredient which causes an adversely modifying effect to the fungi to be controlled, e.g., causing deviations from natural development, killing, effecting regulation, causing desiccation, causing retardation, and the like.

As used herein, herbicide means a compound, e.g., active ingredient that kills, controls or otherwise adversely modifies the growth of plants or undesirable vegetation.

As used herein, a herbicidally effective or vegetation controlling amount is an amount of active ingredient which causes an adversely modifying effect to the vegetation, e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide and fungicide combinations or compositions. Methods of application include, but are not limited to applications to the vegetation or locus thereof, e.g., application to the area adjacent to the vegetation, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines. Exemplary cations include sodium, potassium, magnesium, and ammonium cations of the formula:

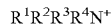

$R^1R^2R^3R^4N^+$ wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising a herbicidally effective amount of (a) a compound of the formula (I)

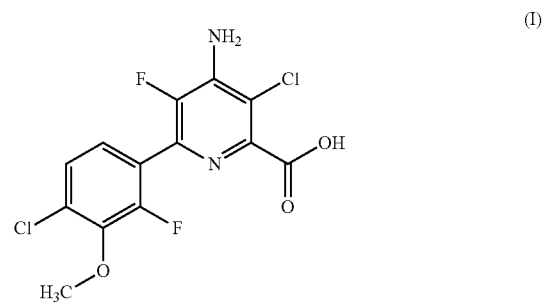 [SMILES: COc1c(Cl)ccc(-c2nc(C(=O)O)c(Cl)c(N)c2F)c1F]

or an agriculturally acceptable salt or ester of thereof, and (b) fungicides, including but not limited to, azoxystrobin, carbendazim, difenoconazole, flutolanil, hexaconazole, iprobenfos, isoprothiolane, isotianil, kasugamycin, mancozeb, myclobutanil, phthalide, probenazole, propiconazole, pyroquilon, tebuconazole, thifluzamide, tricyclazole, trifloxystrobin, validamycin, and a compound of formula (II).

Provided herein are also methods of controlling undesirable vegetation comprising contacting the vegetation or locus thereof, i.e., the area adjacent to the vegetation with or applying to the soil or water to prevent the emergence or growth of vegetation a herbicidally effective amount of the compound of formula (I) or agriculturally acceptable salt or ester thereof and (b) fungicides, including but not limited to, azoxystrobin, carbendazim, difenoconazole, flutolanil, hexaconazole, iprobenfos, isoprothiolane, isotianil, kasugamycin, mancozeb, myclobutanil, phthalide, probenazole, propiconazole, pyroquilon, tebuconazole, thifluzamide, tricyclazole, trifloxystrobin, validamycin, and a compound of formula (II). In certain embodiments, the methods employ the compositions described herein.

Furthermore, in some embodiments, the combination of compound (I) or agriculturally acceptable salt or ester thereof and azoxystrobin, carbendazim, difenoconazole, flutolanil, hexaconazole, iprobenfos, isoprothiolane, isotianil, kasugamycin, mancozeb, myclobutanil, phthalide, probenazole, propiconazole, pyroquilon, tebuconazole, thifluzamide, tricyclazole, trifloxystrobin, validamycin, or a compound of formula (II) exhibits synergism, e.g., the herbicidal activity is more effective in combination than when the compound of formula (I) is applied individually. Synergism has been defined as "an interaction of two or more factors such that the effect when combined is greater than the predicted effect based on the response of each factor applied separately." Senseman, S., Ed. Herbicide Handbook. 9$^{th}$ ed. Lawrence: Weed Science Society of America, 2007. In certain embodiments, the compositions exhibit synergy as determined by the Colby's equation. Colby, S. R. Calculation of the synergistic and antagonistic response of herbicide combinations. Weeds 1967, 15, 20-22.

In certain embodiments of the compositions and methods described herein, the compound of formula (I), i.e., the carboxylic acid, is employed. In certain embodiments, a carboxylate salt of the compound of formula (I) is employed.

In certain embodiments, an arylalkyl or alkyl ester is employed. In certain embodiments, a benzyl, substituted benzyl, or $C_1$-$C_4$ alkyl, e.g., n-butyl ester is employed. In certain embodiments, the benzyl ester is employed.

In some embodiments, the compound of formula (I) or salt or ester thereof and azoxystrobin, carbendazim, difenoconazole, flutolanil, hexaconazole, iprobenfos, isoprothiolane, isotianil, kasugamycin, mancozeb, myclobutanil, phthalide, probenazole, propiconazole, pyroquilon, tebuconazole, thifluzamide, tricyclazole, trifloxystrobin, validamycin, or a compound of formula (II) are formulated in one composition, tank mixed, applied simultaneously, or applied sequentially.

Herbicidal activity is exhibited by the compounds when they are applied directly to the plant or to the area adjacent to the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, *sorghum*, corn/maize, sugarcane, sunflower, oilseed rape, canola, sugar beet, soybean, cotton, pineapple, pastures, grasslands, rangelands, fallowland, turf, tree and vine orchards, plantation crops, vegetables, industrial vegetation management (IVM) and rights-of-way (ROW).

In certain embodiments, the compositions and methods provided herein are utilized to control weeds in rice. In certain embodiments, the rice is direct-seeded, water-seeded, or transplanted rice.

The compositions and methods described herein may be used to control undesirable vegetation in glyphosate-tolerant-, 5-enolpyruvylshikimate-3-phosphate (EP SP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant- and bromoxynil-tolerant-crops (such as, but not limited to, soybean, cotton, canola/oilseed rape, rice, cereals, corn, *sorghum*, sunflower, sugar beet, sugarcane, turf, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in crops possessing multiple or stacked traits conferring tolerance to multiple chemistries and/or inhibitors of multiple modes-of-action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in rice, cereals, wheat, barley, oats, rye, *sorghum*, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights-of-way (ROW).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schuh. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Oryza* species (red and weedy rice, ORYSS), *Panicum dichotomiflorum* (L.) Michx. (fall *panicum*, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* Poir. (southeastern primrosewillow, LUDLI), *Ludwigia octovalvis* (Jacq.) Raven (longfruited primrose-willow, LUDOC), *Monochoria korsakowii* Regel & Maack (*monochoria*, MOOKA), *Monochoria vaginalis* (Berm. F.) C. Presl ex Kuhth, (*monochoria*, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum* hydropiperoides Michx. (mild smartweed, POLHP), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp *sesbania*, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (*kochia*, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly *sida*, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops, and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred *anoda*, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC., *Spermacoce alata* Aubl., or *Spermacose latifolia* (broadleaf button weed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA), *Conyza sumatrensis* (Retz.) E. H. Walker (tall fleabane, ERIFL), *Helianthus annuus* L. (common sunflower, HELAN), *Jacquemontia tamnifolia*

(L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (sida, SIDSS), *Sida spinosa* L. (prickly sida, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kyllinga* species (kyllinga, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhorn/narrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation consisting of grass, broadleaf and sedge weeds. In certain embodiments, the compositions and methods provided herein are utilized to control undesirable grass, broadleaf and sedge vegetation including but not limited to *Brachiaria/Urochloa*, *Cyperus*, *Digitaria*, *Echinochloa*, *Fimbristylis*, *Ipomoea*, *Leptochloa*, *Oryza*, and *Schoenoplectus*.

In some embodiments, the combination of compound (I) or agriculturally acceptable ester or salt thereof and fungicides are used to control, including but not limited to, broadleaf signalgrass (*Brachiaria platyphylla* (Groseb.) Nash), yellow nutsedge (*Cyperus esculentus* L.), rice flatsedge (*Cyperus iria* L.), purple nutsedge (*Cyperus rotundus*), large crabgrass (*Digitaria sanguinalis*), barnyardgrass (*Echinochloa crus-galli*), jungle rice (*Echinochloa colonum*), watergrass (*Echinochloa oryzoides*), globe fringerush (*Fimbristylis miliacea* (L.) Vahl), ivyleaf morningglory (*Ipomoea hederacea*), Chinese sprangletop (*Leptochloa chinensis*), red rice (*Oryza sativa*), and Japanese bulrush (*Schoenoplectus juncoides*).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EP SP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutanamides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, and biotypes with resistance or tolerance to multiple herbicide modes-of-action, and biotypes with multiple resistance or tolerance mechanisms (e.g., target site resistance or metabolic resistance).

In certain embodiments of the compositions and methods described herein, the compound of formula (I) or salt or ester thereof is used in combination with azoxystrobin. With respect to the compositions, in some embodiments, the weight ratio of the compound of formula (I) or salt or ester thereof to azoxystrobin is within the range of from about 1:500 to about 12:1. In certain embodiments, the weight ratio of the compound of formula (I) or salt or ester thereof to azoxystrobin is within the range of from about 1:57 to about 1:2. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 grams active ingredient per hectare (g ai/ha) to about 1300 g ai/ha based on the total amount of active ingredients in the composition. In certain embodiments, the composition is applied at an application rate of from about 66 g ai/ha to about 300 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and azoxystrobin, e.g., sequentially or simultaneously. In some embodiments, azoxystrobin is applied at a rate from about 25 g ai/ha to about 1000 g ai/ha and the compound of formula (I) or salt or ester thereof is applied at a rate from about 2 grams acid equivalent per hectare (g ae/ha) to about 300 g ae/ha. In some embodiments, azoxystrobin is applied at a rate from about 62 g ai/ha to about 250 g ai/ha and the compound of formula (I) or salt or ester thereof is applied at a rate from about 4 g ae/ha to about 32 g ae/ha. In certain embodiments, the methods utilize the compound of formula (I) or its benzyl ester and azoxystrobin. In one embodiment, the methods utilize the compound of formula (I) and azoxystrobin, wherein the compound of formula (I) is applied at a rate of from about 3 g ae/ha to about 200 g ae/ha, and azoxystrobin is applied at a rate of from about 30 g ai/ha to about 900 g ai/ha. In one embodiment, the methods utilize the benzyl ester of the compound of formula (I) and azoxystrobin, wherein the benzyl ester of the compound of formula (I) is applied at a rate of from about 4.4 g ae/ha to about 32 g ae/ha, and azoxystrobin is applied at a rate of from about 62 g ai/ha to about 250 g ai/ha.

In certain embodiments of the compositions and methods described herein, the compound of formula (I) or salt or ester thereof is used in combination with carbendazim. With respect to the compositions, in some embodiments, the weight ratio of the compound of formula (I) or salt or ester thereof to carbendazim is within the range of from about 1:375 to about 12:1. In certain embodiments, the weight ratio of the compound of formula (I) or salt or ester thereof to carbendazim is within the range of from about 1:31 to about 1:4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 g ai/ha to about 1,050 g ai/ha based on the total amount of active ingredients in the composition. In certain embodiments, the composition is applied at an application rate of from about 133 g ai/ha to about 282 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and carbendazim, e.g., sequentially or simultaneously. In some embodiments, carbendazim is applied at a rate from about 25 g ai/ha to about 750 g ai/ha and the compound of formula (I) or salt or ester thereof is applied at a rate from about 2 g ae/ha to about 300 g ae/ha. In some embodiments, carbendazim is applied at a rate from about 50 g ai/ha to about 600 g ai/ha and the compound of formula (I) or salt or ester thereof is applied at a rate from about 3 g ae/ha to about 200 g ae/ha. In certain embodiments, the methods utilize the compound of formula (I) or its benzyl ester and carbendazim. In one embodiment, the methods utilize the compound of formula (I) and carbendazim, wherein the compound of formula (I) is applied at a rate of from about 3 g ae/ha to about 200 g ae/ha, and carbendazim is applied at a rate of from about 50 g ai/ha to about 600 g ai/ha. In one embodiment, the methods utilize the benzyl ester of the compound of formula (I) and carbendazim wherein the benzyl ester of the compound of formula (I) is applied at a rate of from about 8 g ae/ha to about 32 g ae/ha, and carbendazim is applied at a rate of from about 125 g ai/ha to about 250 g ai/ha.

In certain embodiments of the compositions and methods described herein, the compound of formula (I) or salt or ester thereof is used in combination with difenoconazole. With respect to the compositions, in some embodiments, the weight ratio of the compound of formula (I) or salt or ester thereof to difenoconazole is within the range of from about 1:250 to about 12:1. In certain embodiments, the weight ratio of the compound of formula (I) or salt or ester thereof to difenoconazole is within the range of from about 1:46 to about 1:1.5. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 g ai/ha to about 800 g ai/ha based on the total amount of active ingredients in the composition. In certain embodiments, the composition is applied at an application rate of from about 54 g ai/ha to about 250 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and difenoconazole, e.g., sequentially or simultaneously. In some embodiments, difenoconazole is applied at a rate from about 25 g ai/ha to about 500 g ai/ha and the compound of formula (I) or salt or ester thereof is applied at a rate from about 2 g ae/ha to about 300 g ae/ha. In some embodiments, difenoconazole is applied at a rate from about 50 g ai/ha to about 200 g ai/ha and the compound of formula (I) or salt or ester thereof is applied at a rate from about 8 g ae/ha to about 32 g ae/ha. In certain embodiments, the methods utilize the compound of formula (I) or its benzyl ester and difenoconazole. In one embodiment, the methods utilize the compound of formula (I) and difenoconazole, wherein the compound of formula (I) is applied at a rate of from about 3 g ae/ha to about 200 g ae/ha, and difenoconazole is applied at a rate of from about 30 g ai/ha to about 450 g ai/ha. In one embodiment, the methods utilize the benzyl ester of the compound of formula (I) and difenoconazole, wherein the benzyl ester of the compound of formula (I) is applied at a rate of from about 8 g ae/ha to about 32 g ae/ha, and difenoconazole is applied at a rate of from about 50 g ai/ha to about 200 g ai/ha.

In certain embodiments of the compositions and methods described herein, the compound of formula (I) or salt or ester thereof is used in combination with flutolanil. With respect to the compositions, in some embodiments, the weight ratio of the compound of formula (I) or salt or ester thereof to flutolanil is within the range of from about 1:500 to about 12:1. In certain embodiments, the weight ratio of the compound of formula (I) or salt or ester thereof to flutolanil is within the range of from about 1:70 to about 1:4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 g ai/ha to about 1,300 g ai/ha based on the total amount of active ingredients in the composition. In certain embodiments, the composition is applied at an application rate of from about 148 g ai/ha to about 592 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and flutolanil, e.g., sequentially or simultaneously. In some embodiments, flutolanil is applied at a rate from about 25 g ai/ha to about 1,000 g ai/ha and the compound of formula (I) or salt or ester thereof is applied at a rate from about 2 g ae/ha to about 300 g ae/ha. In some embodiments, flutolanil is applied at a rate from about 50 g ai/ha to about 900 g ai/ha and the compound of formula (I) or salt or ester thereof is applied at a rate from about 3 g ae/ha to about 200 g ae/ha. In certain embodiments, the methods utilize the compound of formula (I) or its benzyl ester and flutolanil. In one embodiment, the methods utilize the compound of formula (I) and flutolanil, wherein the compound of formula (I) is applied at a rate of from about 3 g ae/ha to about 200 g ae/ha, and flutolanil is applied at a rate of from about 50 g ai/ha to about 900 g ai/ha. In one embodiment, the methods utilize the benzyl ester of the compound of formula (I) and flutolanil, wherein the benzyl ester of the compound of formula (I) is applied at a rate of from about 8 g ae/ha to about 32 g ae/ha, and flutolanil is applied at a rate of from about 140 g ai/ha to about 560 g ai/ha.

In certain embodiments of the compositions and methods described herein, the compound of formula (I) or salt or ester thereof is used in combination with hexaconazole. With respect to the compositions, in some embodiments, the weight ratio of the compound of formula (I) or salt or ester thereof to hexaconazole is within the range of from about 1:250 to about 60:1. In certain embodiments, the weight ratio of the compound of formula (I) or salt or ester thereof to hexaconazole is within the range of from about 1:12.5 to about 1.25:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 7 g ai/ha to about 800 g ai/ha based on the total amount of active ingredients in the composition. In certain embodiments, the composition is applied at an application rate of from about 33 g ai/ha to about 150 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and hexaconazole, e.g., sequentially or simultaneously. In some embodiments, hexaconazole is applied at a rate from about 5 g ai/ha to about 500 g ai/ha and the compound of formula (I) or salt or ester thereof is applied at a rate from about 2 g ae/ha to about 300 g ae/ha. In some embodiments, hexaconazole is applied at a rate from about 25 g ai/ha to about 100 g ai/ha and the compound of formula (I) or salt or ester thereof is applied at a rate from about 8 g ae/ha to about 32 g ae/ha. In certain embodiments, the methods utilize the compound of formula (I) or its benzyl ester and hexaconazole. In one embodiment, the methods utilize the compound of formula (I) and hexaconazole, wherein the compound of formula (I) is applied at a rate of from about 3 g ae/ha to about 200 g ae/ha, and hexaconazole is applied at a rate of from about 7 g ai/ha to about 475 g ai/ha. In one embodiment, the methods utilize the benzyl ester of the compound of formula (I) and hexaconazole, wherein the benzyl ester of the compound of formula (I) is applied at a rate of from about 8 g ae/ha to about 32 g ae/ha, and hexaconazole is applied at a rate of from about 25 g ai/ha to about 100 g ai/ha.

In certain embodiments of the compositions and methods described herein, the compound of formula (I) or salt or ester thereof is used in combination with iprobenfos. With respect to the compositions, in some embodiments, the weight ratio of the compound of formula (I) or salt or ester thereof to iprobenfos is within the range of from about 1:1,000 to about 3:1. In certain embodiments, the weight ratio of the compound of formula (I) or salt or ester thereof to iprobenfos is within the range of from about 1:600 to about 1:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 102 g ai/ha to about 2,300 g ai/ha based on the total amount of active ingredients in the composition. In certain embodiments, the composition is applied at an application rate of from about 113 g ai/ha to about 1,950 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and iprobenfos, e.g., sequentially or simultaneously. In some embodiments, iprobenfos is applied at a rate from about 100 g ai/ha to about 2,000 g ai/ha and the compound of formula (I) or salt or ester thereof is applied at a rate from about 2 g ae/ha to about 300 g ae/ha. In some embodiments, iprobenfos is applied at a rate from about 200 g ai/ha to about 1,900 g ai/ha and the compound of formula (I) or salt or ester thereof is applied at a rate from about 3 g ae/ha to about 200 g ae/ha. In certain embodiments, the methods utilize the compound of formula (I) or its benzyl ester and iprobenfos. In one embodiment, the methods utilize the compound of formula (I) and iprobenfos wherein the compound of formula (I) is applied at a rate of from about 3 g ae/ha to about 200 g ae/ha, and iprobenfos is applied at a rate of from about 200 g ai/ha to about 1,900 g ai/ha. In one embodiment, the methods utilize the benzyl ester of the compound of formula (I) and iprobenfos, wherein the benzyl ester of the compound of formula (I) is applied at a rate of from about 3 g ae/ha to about 150 g ae/ha, and iprobenfos is applied at a rate of from about 110 g ai/ha to about 1,800 g ai/ha.

In certain embodiments of the compositions and methods described herein, the compound of formula (I) or salt or ester thereof is used in combination with isoprothiolane. With respect to the compositions, in some embodiments, the weight ratio of the compound of formula (I) or salt or ester thereof to isoprothiolane is within the range of from about 1:500 to about 6:1. In certain embodiments, the weight ratio of the compound of formula (I) or salt or ester thereof to isoprothiolane is within the range of from about 1:300 to about 2:1. In certain embodiments, the weight ratio of the compound of formula (I) or salt or ester thereof to isoprothiolane is within the range of from about 1:67 to about 1:6. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 g ai/ha to about 1,300 g ai/ha based on the total amount of active ingredients in the composition. In certain embodiments, the composition is applied at an application rate of from about 100 g ai/ha to about 1,100 g ai/ha based on the total amount of active ingredients in the composition. In certain embodiments, the composition is applied at an application rate of from about 200 g ai/ha to about 600 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and isoprothiolane, e.g., sequentially or simultaneously. In some embodiments, isoprothiolane is applied at a rate from about 50 g ai/ha to about 1,000 g ai/ha and the compound of formula (I) or salt or ester thereof is applied at a rate from about 2 g ae/ha to about 300 g ae/ha. In some embodiments, isoprothiolane is applied at a rate from about 75 g ai/ha to about 950 g ai/ha and the compound of formula (I) or salt or ester thereof is applied at a rate from about 3 g ae/ha to about 200 g ae/ha. In some embodiments, isoprothiolane is applied at a rate from about 200 g ai/ha to about 533 g ai/ha and the compound of formula (I) or salt or ester thereof is applied at a rate from about 8 g ae/ha to about 32 g ae/ha. In certain embodiments, the methods utilize the compound of formula (I) or its benzyl ester and isoprothiolane. In one embodiment, the methods utilize the compound of formula (I) and isoprothiolane, wherein the compound of formula (I) is applied at a rate of from about 3 g ae/ha to about 200 g ae/ha, and isoprothiolane is applied at a rate of from about 75 g ai/ha to about 950 g ai/ha. In one embodiment, the methods utilize the benzyl ester of the compound of formula (I) and isoprothiolane, wherein the benzyl ester of the compound of formula (I) is applied at a rate of from about 3 g ae/ha to about 150 g ae/ha, and isoprothiolane is applied at a rate of from about 70 g ai/ha to about 900 g ai/ha. In one embodiment, the methods utilize the benzyl ester of the compound of formula (I) and isoprothiolane, wherein the benzyl ester of the compound of formula (I) is applied at a rate of from about 8 g ae/ha to about 32 g ae/ha, and isoprothiolane is applied at a rate of from about 200 g ai/ha to about 600 g ai/ha.

In certain embodiments of the compositions and methods described herein, the compound of formula (I) or salt or ester thereof is used in combination with isotianil. With respect to the compositions, in some embodiments, the weight ratio of the compound of formula (I) or salt or ester thereof to isotianil is within the range of from about 1:500 to about 30:1. In certain embodiments, the weight ratio of the compound of formula (I) or salt or ester thereof to isotianil is within the range of from about 1:48 to about 1:3. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 g ai/ha to about 1,300 g ai/ha based on the total amount of active ingredients in the composition. In certain embodiments, the composition is applied at an application rate of from about 108 g ai/ha to about 420 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and isotianil, e.g., sequentially or simultaneously. In some embodiments, isotianil is applied at a rate from about 10 g ai/ha to about 1,000 g ai/ha and the compound of formula (I) or salt or ester thereof is applied at a rate from about 2 g ae/ha to about 300 g ae/ha. In some embodiments, isotianil is applied at a rate from about 25 g ai/ha to about 380 g ai/ha and the compound of formula (I) or salt or ester thereof is applied at a rate from about 8 g ae/ha to about 32 g ae/ha. In certain embodiments, the methods utilize the compound of formula (I) or its benzyl ester and isotianil. In one embodiment, the methods utilize the compound of formula (I) and isotianil, wherein the compound of formula (I) is applied at a rate of from about 3 g ae/ha to about 200 g ae/ha, and isotianil is applied at a rate of from about 25 g ai/ha to about 700 g ai/ha. In one embodiment, the methods utilize the benzyl ester of the compound of formula (I) and isotianil, wherein the benzyl ester of the compound of formula (I) is applied at a rate of from about 8 g ae/ha to about 32 g ae/ha, and isotianil is applied at a rate of from about 100 g ai/ha to about 380 g ai/ha.

In certain embodiments of the compositions and methods described herein, the compound of formula (I) or salt or ester thereof is used in combination with kasugamycin. With respect to the compositions, in some embodiments, the weight ratio of the compound of formula (I) or salt or ester thereof to kasugamycin is within the range of from about 1:250 to about 150:1. In certain embodiments, the weight ratio of the compound of formula (I) or salt or ester thereof to kasugamycin is within the range of from about 1:9 to about 2:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 g ai/ha to about 800 g ai/ha based on the total amount of active ingredients in the composition. In certain embodiments, the composition is applied at an application rate of from about 25 g ai/ha to about 105 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and kasugamycin, e.g., sequentially or simultaneously. In some embodiments, kasugamycin is applied at a rate from about 2 g ai/ha to about 500 g ai/ha and the compound of formula (I) or salt or ester thereof is applied at a rate from about 2 g ae/ha to about 300 g ae/ha. In some embodiments, kasugamycin is applied at a rate from about 4 g ai/ha to about 450 g ai/ha and the compound of formula (I) or salt or ester thereof is applied at a rate from about 3 g ae/ha to about 200 g ae/ha. In certain embodiments, the methods utilize the compound of formula (I) or its benzyl ester and kasugamycin. In one embodiment, the methods utilize the compound of formula (I) and kasugamycin wherein the compound of formula (I) is applied at a rate of from about 3 g ae/ha to about 200 g ae/ha, and kasugamycin is applied at a rate of from about 4 g ai/ha to about 450 g ai/ha. In one embodiment, the methods utilize the benzyl ester of the compound of formula (I) and kasugamycin, wherein the benzyl ester of the compound of formula (I) is applied at a rate of from about 8 g ae/ha to about 32 g ae/ha, and kasugamycin is applied at a rate of from about 17.5 g ai/ha to about 70 g ai/ha.

In certain embodiments of the compositions and methods described herein, the compound of formula (I) or salt or ester thereof is used in combination with mancozeb. With respect to the compositions, in some embodiments, the weight ratio of the compound of formula (I) or salt or ester thereof to mancozeb is within the range of from about 1:2,500 to about 12:1. In certain embodiments, the weight ratio of the compound of formula (I) or salt or ester thereof to mancozeb is within the range of from about 1:210 to about 1:26. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 g ai/ha to about 5,300 g ai/ha based on the total amount of active ingredients in the composition. In certain embodiments, the composition is applied at an application rate of from about 848 g ai/ha to about 1,712 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and mancozeb, e.g., sequentially or simultaneously. In some embodiments, mancozeb is applied at a rate from about 25 g ai/ha to about 5,000 g ai/ha and the compound of formula (I) or salt or ester thereof is applied at a rate from about 2 gae/ha to about 300 g ae/ha. In some embodiments, mancozeb is applied at a rate from about 50 g ai/ha to about 4,500 g ai/ha and the compound of formula (I) or salt or ester thereof is applied at a rate from about 3 g ae/ha to about 200 g ae/ha. In certain embodiments, the methods utilize the compound of formula (I) or its benzyl ester and mancozeb. In one embodiment, the methods utilize the compound of formula (I) and mancozeb, wherein the compound of formula (I) is applied at a rate of from about 3 g ae/ha to about 200 g ae/ha, and mancozeb is applied at a rate of from about 50 g ai/ha to about 4,500 g ai/ha. In one embodiment, the methods utilize the benzyl ester of the compound of formula (I) and mancozeb, wherein the benzyl ester of the compound of formula (I) is applied at a rate of from about 8 g ae/ha to about 32 g ae/ha, and mancozeb is applied at a rate of from about 840 g ai/ha to about 1,680 g ai/ha.

In certain embodiments of the compositions and methods described herein, the compound of formula (I) or salt or ester thereof is used in combination with myclobutanil. With respect to the compositions, in some embodiments, the weight ratio of the compound of formula (I) or salt or ester thereof to myclobutanil is within the range of from about 1:250 to about 12:1. In certain embodiments, the weight ratio of the compound of formula (I) or salt or ester thereof to myclobutanil is within the range of from about 1:38 to about 1:1.5. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 22 g ai/ha to about 800 g ai/ha based on the total amount of active ingredients in the composition. In certain embodiments, the composition is applied at an application rate of from about 55 g ai/ha to about 232 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and myclobutanil, e.g., sequentially or simultaneously. In some embodiments, myclobutanil is applied at a rate from about 25 g ai/ha to about 500 g ai/ha and the compound of formula (I) or salt or ester thereof is applied at a rate from about 2 g ae/ha to about 300 g ae/ha. In some embodiments, myclobutanil is applied at a rate from about 50 g ai/ha to about 200 g ai/ha and the compound of formula (I) or salt or ester thereof is applied at a rate from about 5 g ae/ha to about 32 g ae/ha. In certain embodiments, the methods utilize the compound of formula (I) or its benzyl ester and myclobutanil. In one embodiment, the methods utilize the compound of formula (I) and myclobutanil, wherein the compound of formula (I) is applied at a rate of from about 3 g ae/ha to about 200 g ae/ha, and myclobutanil is applied at a rate of from about 50 g ai/ha to about 450 g ai/ha. In one embodiment, the methods utilize the benzyl ester of the compound of formula (I) and myclobutanil, wherein the benzyl ester of the compound of formula (I) is applied at a rate of from about 5 g ae/ha to about 32 g ae/ha, and myclobutanil is applied at a rate of from about 50 g ai/ha to about 200 g ai/ha.

In certain embodiments of the compositions and methods described herein, the compound of formula (I) or salt or ester thereof is used in combination with phthalide. With respect to the compositions, in some embodiments, the weight ratio of the compound of formula (I) or salt or ester thereof to phthalide is within the range of from about 1:500 to about 15:1. In certain embodiments, the weight ratio of the compound of formula (I) or salt or ester thereof to phthalide is within the range of from about 1:267 to about 5:1. In certain embodiments, the weight ratio of the compound of formula (I) or salt or ester thereof to phthalide is within the range of from about 1:38 to about 1:3. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 22 g ai/ha to about 1,300 g ai/ha based on the total amount of active ingredients in the composition. In certain embodiments, the composition is applied at an application rate of from about 33 g ai/ha to about 950 g ai/ha based on the total amount of active ingredients in the composition. In certain embodiments, the composition is applied at an application rate of from about 100 g ai/ha to about 350 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and phthalide, e.g., sequentially or simultaneously. In some embodiments, phthalide is applied at a rate from about 20 g ai/ha to about 1,000 g ai/ha and the compound of formula (I) or salt or ester thereof is applied at a rate from about 2 g ae/ha to about 300 g ae/ha. In some embodiments, phthalide is applied at a rate from about 25 g ai/ha to about 950 g ai/ha and the compound of formula (I) or salt or ester thereof is applied at a rate from about 3 g ae/ha to about 200 g ae/ha. In some embodiments, phthalide is applied at a rate from about 100 g ai/ha to about 300 g ai/ha and the compound of formula (I) or salt or ester thereof is applied at a rate from about 8 g ae/ha to about 32 g ae/ha. In certain embodiments, the methods utilize the compound of formula (I) or its benzyl ester and phthalide. In one embodiment, the methods utilize the compound of formula (I) and phthalide, wherein the compound of formula (I) is applied at a rate of from about 3 g ae/ha to about 200 g ae/ha, and phthalide is applied at a rate of from about 25 g ai/ha to about 950 g ai/ha. In one embodiment, the methods utilize the benzyl ester of the compound of formula (I) and phthalide, wherein the benzyl ester of the compound of formula (I) is applied at a rate of from about 3 g ae/ha to about 150 g ae/ha, and phthalide is applied at a rate of from about 30 g ai/ha to about 800 g ai/ha. In one embodiment, the methods utilize the benzyl ester of the compound of formula (I) and phthalide, wherein the benzyl ester of the compound of formula (I) is applied at a rate of from about 8 g ae/ha to about 32 g ae/ha, and phthalide is applied at a rate of from about 100 g ai/ha to about 300 g ai/ha.

In certain embodiments of the compositions and methods described herein, the compound of formula (I) or salt or ester thereof is used in combination with probenazole. With respect to the compositions, in some embodiments, the weight ratio of the compound of formula (I) or salt or ester thereof to probenazole is within the range of from about 1:2,500 to about 6:1. In certain embodiments, the weight ratio of the compound of formula (I) or salt or ester thereof to probenazole is within the range of from about 1:500 to about 1:10. In certain embodiments, the weight ratio of the compound of formula (I) or salt or ester thereof to probenazole is within the range of from about 1:500 to about 1:15. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 g ai/ha to about 5,300 g ai/ha based on the total amount of active ingredients in the composition. In certain embodiments, the composition is applied at an application rate of from about 103 g ai/ha to about 4,050 g ai/ha based on the total amount of active ingredients in the composition. In certain embodiments, the composition is applied at an application rate of from about 500 g ai/ha to about 4,000 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and probenazole, e.g., sequentially or simultaneously. In some embodiments, probenazole is applied at a rate from about 50 g ai/ha to about 5,000 g ai/ha and the compound of formula (I) or salt or ester thereof is applied at a rate from about 2 g ae/ha to about 300 g ae/ha. In some embodiments, probenazole is applied at a rate from about 75 g ai/ha to about 4,500 g ai/ha and the compound of formula (I) or salt or ester thereof is applied at a rate from about 3 g ae/ha to about 200 g ae/ha. In some embodiments, probenazole is applied at a rate from about 500 g ai/ha to about 4,000 g ai/ha and the compound of formula (I) or salt or ester thereof is applied at a rate from about 8 g ae/ha) to about 32 g ae/ha. In certain embodiments, the methods utilize the compound of formula (I) or its benzyl ester and probenazole. In one embodiment, the methods utilize the compound of formula (I) and probenazole, wherein the compound of formula (I) is applied at a rate of from about 3 g ae/ha to about 200 g ae/ha, and probenazole is applied at a rate of from about 75 g ai/ha to about 4,500 g ai/ha. In one embodiment, the methods utilize the benzyl ester of the compound of formula (I) and probenazole wherein the benzyl ester of the compound of formula (I) is applied at a rate of from about 8 g ae/ha to about 50 g ae/ha, and probenazole is applied at a rate of from about 500 g ai/ha to about 4,000 g ai/ha. In one embodiment, the methods utilize the benzyl ester of the compound of formula (I) and probenazole wherein the benzyl ester of the compound of formula (I) is applied at a rate of from about 8 g ae/ha to about 32 g ae/ha, and probenazole is applied at a rate of from about 500 g ai/ha to about 4,000 g ai/ha.

In certain embodiments of the compositions and methods described herein, the compound of formula (I) or salt or ester thereof is used in combination with propiconazole. With respect to the compositions, in some embodiments, the weight ratio of the compound of formula (I) or salt or ester thereof to propiconazole is within the range of from about 1:250 to about 30:1. In certain embodiments, the weight ratio of the compound of formula (I) or salt or ester thereof to propiconazole is within the range of from about 1:47 to about 1:3. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 g ai/ha to about 800 g ai/ha based on the total amount of active ingredients in the composition. In certain embodiments, the composition is applied at an application rate of from about 67 g ai/ha to about 275 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and propiconazole, e.g., sequentially or simultaneously. In some embodiments, propiconazole is applied at a rate from about 10 g ai/ha to about 500 g ai/ha and the compound of formula (I) or salt or ester thereof is applied at a rate from about 2 g ae/ha to about 300 g ae/ha. In some embodiments, propiconazole is applied at a rate from about 20 g ai/ha to about 450 g ai/ha and the compound of formula (I) or salt or ester thereof is applied at a rate from about 3 g ae/ha to about 200 g ae/ha. In certain embodiments, the methods utilize the compound of formula (I) or its benzyl ester and propiconazole. In one embodiment, the methods utilize the compound of formula (I) and propiconazole, wherein the compound of formula (I) is applied at a rate of from about 3 g ae/ha to about 200 g ae/ha, and propiconazole is applied at a rate of from about 20 g ai/ha to about 450 g ai/ha. In one embodiment, the methods utilize the benzyl ester of the compound of formula (I) and propiconazole, wherein the benzyl ester of the compound of formula (I) is applied at a rate of from about 5.3 g ae/ha to about 21.2 g ae/ha, and propiconazole is applied at a rate of from about 62.5 g ai/ha to about 250 g ai/ha.

In certain embodiments of the compositions and methods described herein, the compound of formula (I) or salt or ester thereof is used in combination with pyroquilon. With respect to the compositions, in some embodiments, the weight ratio of the compound of formula (I) or salt or ester thereof to pyroquilon is within the range of from about 1:1,500 to about 3:1. In certain embodiments, the weight ratio of the compound of formula (I) or salt or ester thereof to pyroquilon is within the range of from about 1:933 to about 1:1. In certain embodiments, the weight ratio of the compound of formula (I) or salt or ester thereof to pyroquilon is within the range of from about 1:615 to about 1:28. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 102 g ai/ha to about 3,300 g ai/ha based on the total amount of active ingredients in the composition. In certain embodiments, the composition is applied at an application rate of from about 153 g ai/ha to about 2,950 g ai/ha based on the total amount of active ingredients in the composition. In certain embodiments, the composition is applied at an application rate of from about 800 g ai/ha to about 1,100 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyroquilon, e.g., sequentially or simultaneously. In some embodiments, pyroquilon is applied at a rate from about 100 g ai/ha to about 3,000 g ai/ha and the compound of formula (I) or salt or ester thereof is applied at a rate from about 2 g ae/ha to about 300 g ae/ha. In some embodiments, pyroquilon is applied at a rate from about 75 g ai/ha to about 2,900 g ai/ha and the compound of formula (I) or salt or ester thereof is applied at a rate from about 3 g ae/ha to about 200 g ae/ha. In some embodiments, pyroquilon is applied at a rate from about 900 g ai/ha to about 1,000 g ai/ha and the compound of formula (I) or salt or ester thereof is applied at a rate from about 8 g ae/ha to about 32 g ae/ha. In certain embodiments, the methods utilize the compound of formula (I) or its benzyl ester and pyroquilon. In one embodiment, the methods utilize the compound of formula (I) and pyroquilon, wherein the compound of formula (I) is applied at a rate of from about 3 g ae/ha to about 200 g ae/ha, and pyroquilon is applied at a rate of from about 75 g ai/ha to about 2,900 g ai/ha. In one embodiment, the methods utilize the benzyl ester of the compound of formula (I) and pyroquilon wherein the benzyl ester of the compound of formula (I) is applied at a rate of from about 3 g ae/ha to about 150 g ae/ha, and pyroquilon is applied at a rate of from about 150 g ai/ha to about 2,800 g ai/ha. In one embodiment, the methods utilize the benzyl ester of the compound of formula (I) and pyroquilon wherein the benzyl ester of the compound of formula (I) is applied at a rate of from about 8 g ae/ha to about 32 g ae/ha, and pyroquilon is applied at a rate of from about 900 g ai/ha to about 1,000 g ai/ha.

In certain embodiments of the compositions and methods described herein, the compound of formula (I) or salt or ester thereof is used in combination with tebuconazole. With respect to the compositions, in some embodiments, the weight ratio of the compound of formula (I) or salt or ester thereof to tebuconazole is within the range of from about 1:250 to about 12:1. In certain embodiments, the weight ratio of the compound of formula (I) or salt or ester thereof to tebuconazole is within the range of from about 1:57 to about 1:2. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 27 g ai/ha to about 800 g ai/ha based on the total amount of active ingredients in the composition. In certain embodiments, the composition is applied at an application rate of from about 66 g ai/ha to about 280 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and tebuconazole, e.g., sequentially or simultaneously. In some embodiments, tebuconazole is applied at a rate from about 25 g ai/ha to about 500 g ai/ha and the compound of formula (I) or salt or ester thereof is applied at a rate from about 2 g ae/ha to about 300 g ae/ha. In some embodiments, tebuconazole is applied at a rate from about 60 g ai/ha to about 250 g ai/ha and the compound of formula (I) or salt or ester thereof is applied at a rate from about 4 g ae/ha to about 32 g ae/ha. In certain embodiments, the methods utilize the compound of formula (I) or its benzyl ester and tebuconazole. In one embodiment, the methods utilize the compound of formula (I) and tebuconazole, wherein the compound of formula (I) is applied at a rate of from about 3 g ae/ha to about 200 g ae/ha, and tebuconazole is applied at a rate of from about 50 g ai/ha to about 450 g ai/ha. In one embodiment, the methods utilize the benzyl ester of the compound of formula (I) and tebuconazole, wherein the benzyl ester of the compound of formula (I) is applied at a rate of from about 4 g ae/ha to about 32 g ae/ha, and tebuconazole is applied at a rate of from about 60 g ai/ha to about 250 g ai/ha.

In certain embodiments of the compositions and methods described herein, the compound of formula (I) or salt or ester thereof is used in combination with thifluzamide. With respect to the compositions, in some embodiments, the weight ratio of the compound of formula (I) or salt or ester thereof to thifluzamide is within the range of from about 1:375 to about 30:1. In certain embodiments, the weight ratio of the compound of formula (I) or salt or ester thereof to thifluzamide is within the range of from about 1:38 to about 1:2.5. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 g ai/ha to about 1,050 g ai/ha based on the total amount of active ingredients in the composition. In certain embodiments, the composition is applied at an application rate of from about 83 g ai/ha to about 332 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and thifluzamide, e.g., sequentially or simultaneously. In some embodiments thifluzamide is applied at a rate from about 10 g ai/ha to about 750 g ai/ha and the compound of formula (I) or salt or ester thereof is applied at a rate from about 2 g ae/ha to about 300 g ae/ha. In some embodiments, thifluzamide is applied at a rate from about 20 g ai/ha to about 700 g ai/ha and the compound of formula (I) or salt or ester thereof is applied at a rate from about 3 g ae/ha to about 200 g ae/ha. In certain embodiments, the methods utilize the compound of formula (I) or its benzyl ester and thifluzamide. In one embodiment, the methods utilize the compound of formula (I) and thifluzamide, wherein the compound of formula (I) is applied at a rate of from about 3 g ae/ha to about 200 g ae/ha, and thifluzamide is applied at a rate of from about 20 g ai/ha to about 700 g ai/ha. In one embodiment, the methods utilize the benzyl ester of the compound of formula (I) and thifluzamide, wherein the benzyl ester of the compound of formula (I) is applied at a rate of from about 8 g ae/ha to about 32 g ae/ha, and thifluzamide is applied at a rate of from about 75 g ai/ha to about 300 g ai/ha.

In certain embodiments of the compositions and methods described herein, the compound of formula (I) or salt or ester thereof is used in combination with tricyclazole. With respect to the compositions, in some embodiments, the weight ratio of the compound of formula (I) or salt or ester thereof to tricyclazole is within the range of from about 1:500 to about 15:1. In certain embodiments, the weight ratio of the compound of formula (I) or salt or ester thereof to tricyclazole is within the range of from about 1:170 to about 1:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 22 g ai/ha to about 1,300 g ai/ha based on the total amount of active ingredients in the composition. In certain embodiments, the composition is applied at an application rate of from about 55 g ai/ha to about 800 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and tricyclazole, e.g., sequentially or simultaneously. In some embodiments, tricyclazole is applied at a rate from about 20 g ai/ha to about 1,000 g ai/ha and the compound of formula (I) or salt or ester thereof is applied at a rate from about 2 g ae/ha to about 300 g ae/ha. In some embodiments, tricyclazole is applied at a rate from about 30 g ai/ha to about 750 g ai/ha and the compound of formula (I) or salt or ester thereof is applied at a rate from about 4 g ae/ha) to about 42 g ae/ha. In certain embodiments, the methods utilize the compound of formula (I) or its benzyl ester and tricyclazole. In one embodiment, the methods utilize the compound of formula (I) and tricyclazole, wherein the compound of formula (I) is applied at a rate of from about 3 g ae/ha to about 200 g ae/ha, and tricyclazole is applied at a rate of from about 30 g ai/ha to about 950 g ai/ha. In one embodiment, the methods utilize the benzyl ester of the compound of formula (I) and tricyclazole, wherein the benzyl ester of the compound of formula (I) is applied at a rate of from about 4.4 g ae/ha to about 42.4 g ae/ha, and tricyclazole is applied at a rate of from about 50 g ai/ha to about 750 g ai/ha.

In certain embodiments of the compositions and methods described herein, the compound of formula (I) or salt or ester thereof is used in combination with trifloxystrobin. With respect to the compositions, in some embodiments, the weight ratio of the compound of formula (I) or salt or ester thereof to trifloxystrobin is within the range of from about 1:250 to about 30:1. In certain embodiments, the weight ratio of the compound of formula (I) or salt or ester thereof to trifloxystrobin is within the range of from about 1:38 to about 1:2.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 g ai/ha to about 800 g ai/ha based on the total amount of active ingredients in the composition. In certain embodiments, the composition is applied at an application rate of from about 83 g ai/ha to about 332 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and trifloxystrobin, e.g., sequentially or simultaneously. In some embodiments, trifloxystrobin is applied at a rate from about 10 g ai/ha to about 500 g ai/ha and the compound of formula (I) or salt or ester thereof is applied at a rate from about 2 g ae/ha to about 300 g ae/ha. In some embodiments, trifloxystrobin is applied at a rate from about 20 g ai/ha to about 450 g ai/ha and the compound of formula (I) or salt or ester thereof is applied at a rate from about 3 g ae/ha to about 200 g ae/ha. In certain embodiments, the methods utilize the compound of formula (I) or its benzyl ester and trifloxystrobin. In one embodiment, the methods utilize the compound of formula (I) and trifloxystrobin, wherein the compound of formula (I) is applied at a rate of from about 3 g ae/ha to about 200 g ae/ha, and trifloxystrobin is applied at a rate of from about 20 g ai/ha to about 450 g ai/ha. In one embodiment, the methods utilize the benzyl ester of the compound of formula (I) and trifloxystrobin, wherein the benzyl ester of the compound of formula (I) is applied at a rate of from about 8 g ae/ha to about 32 g ae/ha, and trifloxystrobin is applied at a rate of from about 75 g ai/ha to about 300 g ai/ha.

In certain embodiments of the compositions and methods described herein, the compound of formula (I) or salt or ester thereof is used in combination with validamycin. With respect to the compositions, in some embodiments, the weight ratio of the compound of formula (I) or salt or ester thereof to validamycin is within the range of from about 1:25 to about 3,000:1. In certain embodiments, the weight ratio of the compound of formula (I) or salt or ester thereof to validamycin is within the range of from about 1:13 to about 500:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 2.1 g ai/ha to about 350 g ai/ha based on the total amount of active ingredients in the composition. In certain embodiments, the composition is applied at an application rate of from about 3.3 g ai/ha to about 190 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and validamycin, e.g., sequentially or simultaneously. In some embodiments, validamycin is applied at a rate from about 0.1 g ai/ha to about 50 g ai/ha and the compound of formula (I) or salt or ester thereof is applied at a rate from about 2 g ae/ha to about 300 g ae/ha. In some embodiments, validamycin is applied at a rate from about 0.2 g ai/ha to about 45 g ai/ha and the compound of formula (I) or salt or ester thereof is applied at a rate from about 3 g ae/ha to about 200 g ae/ha. In certain embodiments, the methods utilize the compound of formula (I) or its benzyl ester and validamycin. In one embodiment, the methods utilize the compound of formula (I) and validamycin, wherein the compound of formula (I) is applied at a rate of from about 3 g ae/ha to about 200 g ae/ha, and validamycin is applied at a rate of from about 0.2 g ai/ha to about 45 g ai/ha. In one embodiment, the methods utilize the benzyl ester of the compound of formula (I) and validamycin, wherein the benzyl ester of the compound of formula (I) is applied at a rate of from about 3 g ae/ha to about 150 g ae/ha, and validamycin is applied at a rate of from about 0.3 g ai/ha to about 40 g ai/ha.

In certain embodiments of the compositions and methods described herein, the compound of formula (I) or salt or ester thereof is used in combination with a compound of formula (II). With respect to the compositions, in some embodiments, the weight ratio of the compound of formula (I) or salt or ester thereof to a compound of formula (II) is within the range of from about 1:375 to about 150:1. In certain embodiments, the weight ratio of the compound of formula (I) or salt or ester thereof to a compound of formula (II) is within the range of from about 1:19 to about 1:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 g ai/ha to about 1,050 g ai/ha based on the total amount of active ingredients in the composition. In certain embodiments, the composition is applied at an application rate of from about 45 g ai/ha to about 182 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and a compound of formula (II), e.g., sequentially or simultaneously. In some embodiments, a compound of formula (II) is applied at a rate from about 2 g ai/ha to about 750 g ai/ha and the compound of formula (I) or salt or ester thereof is applied at a rate from about 2 g ae/ha to about 300 g ae/ha. In some embodiments, a compound of formula (II) is applied at a rate from about 5 g ai/ha to about 700 g ai/ha and the compound of formula (I) or salt or ester thereof is applied at a rate from about 3 g ae/ha to about 200 g ae/ha. In certain embodiments, the methods utilize the compound of formula (I) or its benzyl ester and a compound of formula (II). In one embodiment, the methods utilize the compound of formula (I) and a compound of formula (II), wherein the compound of formula (I) is applied at a rate of from about 3 g ae/ha to about 200 g ae/ha, and a compound of formula (II) is applied at a rate of from about 5 g ai/ha to about 700 g ai/ha. In one embodiment, the methods utilize the benzyl ester of the compound of formula (I) and a compound of formula (II), wherein the benzyl ester of the compound of formula (I) is applied at a rate of from about 8 g ae/ha to about 32 g ae/ha, and a compound of formula (II) is applied at a rate of from about 37.5 g ai/ha to about 180 g ai/ha.

In certain embodiments, the methods and compositions utilizing the compound of formula (I) or salt or ester thereof in combination with azoxystrobin, carbendazim, difenoconazole, flutolanil, hexaconazole, iprobenfos, isoprothiolane, isotianil, kasugamycin, mancozeb, myclobutanil, phthalide, probenazole, propiconazole, pyroquilon, tebuconazole, thifluzamide, tricyclazole, trifloxystrobin, validamycin, or a compound of formula (II) are used to control BRAPP, CYPES, CYPIR, CYPRO, DIGSA, ECHCG, ECHCO, ECHOR, FIMMI, IPOHE, LEFCH and SCPJU.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the compositions and methods described herein include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, fluroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halauxifen, halauxifen-methyl, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac-methyl, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, SYN-523, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thifensulfuron-methyl, thiobencarb, tiocarbazil, tioclorim, topramezone, tralkoxydim, triafamone, triallate, triasulfuron, triaziflam, tribenuron, tribenuron-methyl, tricamba, triclopyr choline salt, triclopyr esters and amines, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes-of-action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, maleic hydrazide, gibberellins, gibberellic acid, abscisic acid, ancymidol, fosamine, glyphosine, isopyrimol, jasmonic acid, maleic hydrazide, mepiquat, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, tree and vine orchards, plantation crops, vegetables, and non-crop (ornamentals) settings. In some embodiments, the plant growth regulator is mixed with the compound of formula (I), or mixed with the compound of formula (I) and fungicides to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or the area adjacent to the weeds or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiments about 0.5 to 90 weight percent. Such compositions are, in certain embodiments, diluted with an inert carrier, such as water, before application. The diluted compositions usually applied to weeds or the locus of weeds contain, in certain embodiments, about 0.0006 to 25.0 weight percent active ingredient and in certain embodiments contain about 0.001 to 20.0 weight percent.

The present compositions can be applied to undesirable vegetation (weeds) or the area adjacent to the weeds by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I and II are greenhouse trial results.

Example I

Evaluation of Postemergence Foliar-Applied Herbicidal Mixtures for Weed Control in Direct-Seeded Rice Seeds or nutlets of the desired test plant species were planted in a soil matrix prepared by mixing aloam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters ($cm^2$). When required to ensure good germination and healthy plants, a fungicide treatment and/or other chemical or physical treatment was applied. The plants were grown for 8-22 days in a greenhouse with an approximate 14 hour (h) photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (Compound A), each formulated as an SC (suspension concentrate), and various fungicidal components alone and in combination. Forms of compound A were applied on an acid equivalent basis.

Forms of compound A (compound of formula I) tested include:

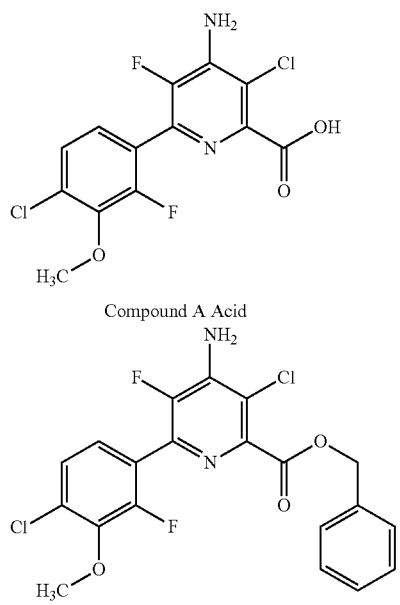

Compound A Acid

Compound A Benzyl Ester

Fungicidal components were applied on an active ingredient basis and consisted of azoxystrobin formulated as Amistar®, carbendazim (technical grade material), difenoconazole formulated as Inspire®, flutolanil (technical grade material), hexaconazole (technical grade material), isoprothiolane (technical grade material), isotianil (technical grade material), kasugamycin (technical grade material), mancozeb formulated as Dithane® M45, myclobutanil formulated as Eagle®, phthalide (technical grade material), probenazole (technical grade material), propiconazole formulated as Tilt®, pyroquilon (technical grade material), tebuconazole formulated as Corail®, thifluzamide (technical grade material), tricyclazole formulated as Beam®, trifloxystrobin (technical grade material), and a compound of formula (II) formulated as an SC.

Treatment requirements were calculated based upon the rates being tested, the concentration of active ingredient or acid equivalent in the formulation and a 12 milliliter (mL) application volume at a rate of 187 liters per hectare (L/ha).

For treatments comprised of formulated compounds, measured amounts of compounds were placed individually in 25 mL glass vials and diluted in a volume of 1.25% volume per volume (v/v) Agri-Dex® crop oil concentrate to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

For treatments comprised of technical compounds, weighed amounts can be placed individually in 25 mL glass vials and dissolved in a volume of 97:3 volume per volume (v/v) acetone/dimethyl sulfoxide (DMSO) to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials were placed individually in 25 mL glass vials and dissolved in a volume of 97:3 v/v acetone/DMSO to obtain 12× stock solutions, and measured amounts of the formulated compounds were placed individually in 25 mL glass vials and diluted in a volume of 1.5% (v/v) crop oil concentrate or water to obtain 12× stock solutions. If a test compound does not dissolve readily, the mixture was warmed and/or sonicated. Application solutions were prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contained 1.25% (v/v) crop oil concentrate. As required, additional water and/or 97:3 v/v acetone/DMSO was added to individual application solutions so that the final acetone and DMSO concentrations of the application solutions being compared were 8.1% and 0.25%, respectively All stock solutions and applications solutions were visually inspected for compound compatibility prior to application. Spray solutions were applied to the plant material with an overhead Mandel track sprayer equipped with 8002E nozzles calibrated to deliver 187 L/ha over an application area of 0.503 square meters ($m^2$) at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture;

B=observed efficacy of active ingredient B at the same concentration as used in the mixture.

The compounds tested, application rates employed, plant species tested, and results are given in Tables 1-25.

TABLE 1

Synergistic Activity of Foliar-Applied Compound A Acid and Azoxystrobin Compositions on Weed Control in a Rice Cropping System.

| Compound A | | Visual Weed Control (%) - 21 DAA | | | |
|---|---|---|---|---|---|
| Acid | Azoxystrobin | DIGSA | | IPOHE | |
| g ae/ha | g ai/ha | Obs | Exp | Obs | Exp |
| 5.3 | 0 | 10 | — | 10 | — |
| 10.6 | 0 | 20 | — | 15 | — |
| 21.2 | 0 | 20 | — | 20 | — |
| 0 | 250 | 0 | — | 0 | — |
| 5.3 | 250 | 30 | 10 | 20 | 10 |
| 10.6 | 250 | 25 | 20 | 30 | 15 |
| 21.2 | 250 | NT | 20 | 25 | 20 |

TABLE 2

Synergistic Activity of Foliar-Applied Compound A Benzyl Ester and Azoxystrobin Compositions on Weed Control in a Rice Cropping System.

| Compound A | | Visual Weed Control (%) - 21 DAA | | | |
|---|---|---|---|---|---|
| Benzyl Ester | Azoxystrobin | DIGSA | | IPOHE | |
| g ae/ha | g ai/ha | Obs | Exp | Obs | Exp |
| 4.38 | 0 | 20 | — | 10 | — |
| 8.75 | 0 | 15 | — | 10 | — |
| 17.5 | 0 | 20 | — | 20 | — |
| 0 | 250 | 0 | — | 0 | — |
| 4.38 | 250 | 20 | 20 | 25 | 10 |
| 8.75 | 250 | 60 | 15 | 15 | 10 |
| 17.5 | 250 | 50 | 20 | 30 | 20 |

| Compound A Benzyl Ester | Azoxystrobin | Visual Weed Control (%) - 22 DAA CYPIR | |
|---|---|---|---|
| g ae/ha | g ai/ha | Obs | Exp |
| 16 | 0 | 73 | — |
| 32 | 0 | 60 | — |
| 0 | 62.5 | 0 | — |
| 0 | 125 | 0 | — |
| 0 | 250 | 0 | — |
| 16 | 62.5 | 100 | 73 |
| 32 | 62.5 | 100 | 60 |
| 16 | 125 | 85 | 73 |
| 32 | 125 | 100 | 60 |
| 16 | 250 | 98 | 73 |
| 32 | 250 | 100 | 60 |

TABLE 2-continued

Synergistic Activity of Foliar-Applied Compound A Benzyl Ester and Azoxystrobin Compositions on Weed Control in a Rice Cropping System.

| Compound A Benzyl Ester | Azoxystrobin | Visual Weed Control (%) - 22 DAA BRAPP | |
|---|---|---|---|
| g ae/ha | g ai/ha | Obs | Exp |
| 8 | 0 | 65 | — |
| 16 | 0 | 70 | — |
| 32 | 0 | 90 | — |
| 0 | 125 | 0 | — |
| 0 | 250 | 0 | — |
| 8 | 125 | 70 | 65 |
| 16 | 125 | 73 | 70 |
| 32 | 125 | 90 | 90 |
| 8 | 250 | 78 | 65 |
| 16 | 250 | 83 | 70 |
| 32 | 250 | 90 | 90 |

| Compound A Benzyl Ester | Azoxystrobin | Visual Weed Control (%) - 21 DAA ECHOR | |
|---|---|---|---|
| g ae/ha | g ai/ha | Obs | Exp |
| 16 | 0 | 43 | — |
| 32 | 0 | 70 | — |
| 0 | 62.5 | 8 | — |
| 0 | 125 | 8 | — |
| 0 | 250 | 5 | — |
| 16 | 62.5 | 40 | 47 |
| 32 | 62.5 | 85 | 72 |
| 16 | 125 | 58 | 47 |
| 32 | 125 | 90 | 72 |
| 16 | 250 | 58 | 45 |
| 32 | 250 | 90 | 72 |

TABLE 3

Synergistic Activity of Foliar-Applied Compound A Benzyl Ester and Carbendazim Compositions on Weed Control in a Rice Cropping System.

| Compound A Benzyl Ester | Carbendazim | Visual Weed Control (%) - 19 DAA ECHCO | |
|---|---|---|---|
| g ae/ha | g ai/ha | Obs | Exp |
| 8 | 0 | 65 | — |
| 16 | 0 | 90 | — |
| 32 | 0 | 95 | — |
| 0 | 125 | 0 | — |
| 0 | 250 | 0 | — |
| 8 | 125 | 85 | 65 |
| 16 | 125 | 95 | 90 |
| 32 | 125 | 99 | 95 |
| 8 | 250 | 95 | 65 |
| 16 | 250 | 95 | 90 |
| 32 | 250 | 95 | 95 |

TABLE 4

Synergistic Activity of Foliar-Applied Compound A Acid and Difenoconazole Compositions on Weed Control in a Rice Cropping System.

| Compound A Acid | Difeno-conazole | Visual Weed Control (%)—21 DAA | | | | | |
|---|---|---|---|---|---|---|---|
| | | DIGSA | | ECHCG | | LEFCH | |
| g ae/ha | g ai/ha | Obs | Exp | Obs | Exp | Obs | Exp |
| 5.3 | 0 | 10 | — | 80 | — | 10 | — |
| 10.6 | 0 | 20 | — | 90 | — | 20 | — |

TABLE 4-continued

Synergistic Activity of Foliar-Applied Compound A Acid and Difenoconazole Compositions on Weed Control in a Rice Cropping System.

| Compound A Acid | Difenoconazole | Visual Weed Control (%)—21 DAA | | | | | |
|---|---|---|---|---|---|---|---|
| | | DIGSA | | ECHCG | | LEFCH | |
| g ae/ha | g ai/ha | Obs | Exp | Obs | Exp | Obs | Exp |
| 21.2 | 0 | 20 | — | 95 | — | 45 | — |
| 0 | 200 | 0 | — | 0 | — | 0 | — |
| 5.3 | 200 | 10 | 10 | 95 | 80 | 50 | 10 |
| 10.6 | 200 | 25 | 20 | 95 | 90 | 30 | 20 |
| 21.2 | 200 | 50 | 20 | 99 | 95 | 40 | 45 |

TABLE 5

Synergistic Activity of Foliar-Applied Compound A Benzyl Ester and Difenoconazole Compositions on Weed Control in a Rice Cropping System.

| Compound A Benzyl Ester | Difenoconazole | Visual Weed Control (%) - 21 DAA | | | |
|---|---|---|---|---|---|
| | | LEFCH | | IPOHE | |
| g ae/ha | g ai/ha | Obs | Exp | Obs | Exp |
| 4.38 | 0 | 10 | — | 10 | — |
| 8.75 | 0 | 20 | — | 10 | — |
| 17.5 | 0 | 55 | — | 20 | — |
| 0 | 200 | 0 | — | 0 | — |
| 4.38 | 200 | 30 | 10 | 10 | 10 |
| 8.75 | 200 | 45 | 20 | 30 | 10 |
| 17.5 | 200 | 50 | 55 | 40 | 20 |

| Compound A Benzyl Ester | Difenoconazole | Visual Weed Control (%) - 22 DAA | |
|---|---|---|---|
| | | DIGSA | |
| g ae/ha | g ai/ha | Obs | Exp |
| 8 | 0 | 15 | — |
| 16 | 0 | 23 | — |
| 32 | 0 | 28 | — |
| 0 | 50 | 0 | — |
| 0 | 100 | 0 | — |
| 0 | 200 | 0 | — |
| 8 | 50 | 25 | 15 |
| 16 | 50 | 28 | 23 |
| 32 | 50 | 45 | 28 |
| 8 | 100 | 40 | 15 |
| 16 | 100 | 53 | 23 |
| 32 | 100 | 55 | 28 |
| 8 | 200 | 55 | 15 |
| 16 | 200 | 53 | 23 |
| 32 | 200 | 68 | 28 |

| Compound A Benzyl Ester | Difenoconazole | Visual Weed Control (%) - 21 DAA | |
|---|---|---|---|
| | | LEFCH | |
| g ae/ha | g ai/ha | Obs | Exp |
| 16 | 0 | 25 | — |
| 32 | 0 | 43 | — |
| 0 | 50 | 0 | — |
| 0 | 100 | 0 | — |
| 0 | 200 | 0 | — |
| 16 | 50 | 30 | 25 |
| 32 | 50 | 53 | 43 |
| 16 | 100 | 33 | 25 |
| 32 | 100 | 60 | 43 |
| 16 | 200 | 48 | 25 |
| 32 | 200 | 70 | 43 |

TABLE 5-continued

Synergistic Activity of Foliar-Applied Compound A Benzyl Ester and Difenoconazole Compositions on Weed Control in a Rice Cropping System.

| Compound A Benzyl Ester | Difenoconazole | Visual Weed Control (%) - 21 DAA | |
|---|---|---|---|
| | | ECHCG | |
| g ae/ha | g ai/ha | Obs | Exp |
| 8 | 0 | 70 | — |
| 16 | 0 | 60 | — |
| 32 | 0 | 90 | — |
| 0 | 50 | 0 | — |
| 0 | 100 | 0 | — |
| 0 | 200 | 0 | — |
| 8 | 50 | 83 | 70 |
| 16 | 50 | 90 | 60 |
| 32 | 50 | 93 | 90 |
| 8 | 100 | 80 | 70 |
| 16 | 100 | 88 | 60 |
| 32 | 100 | 95 | 90 |
| 8 | 200 | 88 | 70 |
| 16 | 200 | 95 | 60 |
| 32 | 200 | 95 | 90 |

| Compound A Benzyl Ester | Difenoconazole | Visual Weed Control (%) - 21 DAA | |
|---|---|---|---|
| | | ECHOR | |
| g ae/ha | g ai/ha | Obs | Exp |
| 8 | 0 | 45 | — |
| 16 | 0 | 43 | — |
| 32 | 0 | 70 | — |
| 0 | 50 | 0 | — |
| 0 | 100 | 0 | — |
| 0 | 200 | 0 | — |
| 8 | 50 | 58 | 45 |
| 16 | 50 | 63 | 43 |
| 32 | 50 | 96 | 70 |
| 8 | 100 | 65 | 45 |
| 16 | 100 | 88 | 43 |
| 32 | 100 | 95 | 70 |
| 8 | 200 | 65 | 45 |
| 16 | 200 | 88 | 43 |
| 32 | 200 | 93 | 70 |

TABLE 6

Synergistic Activity of Foliar-Applied Compound A Benzyl Ester and Flutolanil Compositions on Weed Control in a Rice Cropping System.

| Compound A Benzyl Ester | Flutolanil | Visual Weed Control (%) - 19 DAA | | | |
|---|---|---|---|---|---|
| | | ECHCO | | LEFCH | |
| g ae/ha | g ai/ha | Obs | Exp | Obs | Exp |
| 8 | 0 | 65 | — | 45 | — |
| 16 | 0 | 90 | — | 45 | — |
| 32 | 0 | 95 | — | 50 | — |
| 0 | 280 | 0 | — | 0 | — |
| 0 | 560 | 0 | — | 0 | — |
| 8 | 280 | 85 | 65 | 60 | 45 |
| 16 | 280 | 95 | 90 | 60 | 45 |
| 32 | 280 | 100 | 95 | 70 | 50 |
| 8 | 560 | 90 | 65 | 50 | 45 |
| 16 | 560 | 95 | 90 | 50 | 45 |
| 32 | 560 | 99 | 95 | 55 | 50 |

TABLE 7

Synergistic Activity of Foliar-Applied Compound A Benzyl Ester and Hexaconazole Compositions on Weed Control in a Rice Cropping System.

| Compound A Benzyl Ester | Hexaconazole | Visual Weed Control (%)—21 DAA | | | | | |
|---|---|---|---|---|---|---|---|
| | | ECHCG | | ECHCO | | LEFCH | |
| g ae/ha | g ai/ha | Obs | Exp | Obs | Exp | Obs | Exp |
| 8 | 0 | 45 | — | 50 | — | 25 | — |
| 16 | 0 | 85 | — | 65 | — | 40 | — |
| 32 | 0 | 90 | — | 85 | — | 55 | — |
| 0 | 25 | 0 | — | 0 | — | 0 | — |
| 0 | 50 | 0 | — | 0 | — | 0 | — |
| 0 | 100 | 0 | — | 0 | — | 0 | — |
| 8 | 25 | 80 | 45 | 75 | 50 | 40 | 25 |
| 16 | 25 | 90 | 85 | 90 | 65 | 50 | 40 |
| 32 | 25 | 95 | 90 | 90 | 85 | 65 | 55 |
| 8 | 50 | 80 | 45 | 80 | 50 | 20 | 25 |
| 16 | 50 | 90 | 85 | 85 | 65 | 75 | 40 |
| 32 | 50 | 90 | 90 | 95 | 85 | 60 | 55 |
| 8 | 100 | 85 | 45 | 90 | 50 | 45 | 25 |
| 16 | 100 | 90 | 85 | 90 | 65 | 55 | 40 |
| 32 | 100 | 95 | 90 | 95 | 85 | 60 | 55 |

| Compound A Benzyl Ester | Hexaconazole | Visual Weed Control (%)—21 DAA | | | |
|---|---|---|---|---|---|
| | | BRAPP | | IPOHE | |
| g ae/ha | g ai/ha | Obs | Exp | Obs | Exp |
| 8 | 0 | 55 | — | 10 | — |
| 16 | 0 | 60 | — | 25 | — |
| 0 | 25 | 0 | — | 0 | — |
| 0 | 50 | 0 | — | 0 | — |
| 0 | 100 | 0 | — | 0 | — |
| 8 | 25 | 65 | 55 | 30 | 10 |
| 16 | 25 | 85 | 60 | 35 | 25 |
| 8 | 50 | 50 | 55 | 20 | 10 |
| 16 | 50 | 80 | 60 | 60 | 25 |
| 8 | 100 | 65 | 55 | 20 | 10 |
| 16 | 100 | 65 | 60 | 40 | 25 |

| Compound A Benzyl Ester | Hexaconazole | Visual Weed Control (%)—21 DAA CYPIR | |
|---|---|---|---|
| g ae/ha | g ai/ha | Obs | Exp |
| 8 | 0 | 35 | — |
| 0 | 25 | 0 | — |
| 0 | 50 | 0 | — |
| 0 | 100 | 0 | — |
| 8 | 25 | 80 | 35 |
| 8 | 50 | 60 | 35 |
| 8 | 100 | 50 | 35 |

TABLE 8

Synergistic Activity of Foliar-Applied Compound A Benzyl Ester and Isoprothiolane Compositions on Weed Control in a Rice Cropping System.

| Compound A Benzyl Ester | Isoprothiolane | Visual Weed Control (%) - 21 DAA | | | |
|---|---|---|---|---|---|
| | | LEFCH | | CYPES | |
| g ae/ha | g ai/ha | Obs | Exp | Obs | Exp |
| 8 | 0 | 50 | — | 10 | — |
| 16 | 0 | 60 | — | 90 | — |
| 32 | 0 | 70 | — | 100 | — |
| 0 | 266 | 0 | — | 0 | — |
| 0 | 533 | 0 | — | 0 | — |
| 8 | 266 | 35 | 50 | 90 | 10 |
| 16 | 266 | 40 | 60 | 80 | 90 |
| 32 | 266 | 85 | 70 | 100 | 100 |
| 8 | 533 | 70 | 50 | 100 | 10 |
| 16 | 533 | 80 | 60 | 100 | 90 |
| 32 | 533 | 90 | 70 | 95 | 100 |

| Compound A Benzyl Ester | Isoprothiolane | Visual Weed Control (%) - 21 DAA CYPIR | |
|---|---|---|---|
| g ae/ha | g ai/ha | Obs | Exp |
| 16 | 0 | 85 | — |
| 32 | 0 | 99 | — |
| 0 | 266 | 0 | — |
| 0 | 533 | 0 | — |
| 16 | 266 | 100 | 85 |

TABLE 8-continued

Synergistic Activity of Foliar-Applied Compound
A Benzyl Ester and Isoprothiolane Compositions
on Weed Control in a Rice Cropping System.

| 32 | 266 | 100 | 99 |
| 16 | 533 | 100 | 85 |
| 32 | 533 | 100 | 99 |

TABLE 9

Synergistic Activity of Foliar-Applied Compound A Benzyl Ester and Isotianil Compositions on Weed Control in a Rice Cropping System.

| Compound A Benzyl Ester | Isotianil | Visual Weed Control (%)—20 DAA BRAPP | |
|---|---|---|---|
| g ae/ha | g ai/ha | Obs | Exp |
| 8 | 0 | 60 | — |
| 16 | 0 | 85 | — |
| 32 | 0 | 90 | — |
| 0 | 200 | 0 | — |
| 8 | 200 | 75 | 60 |
| 16 | 200 | 90 | 85 |
| 32 | 200 | 90 | 90 |

| Compound A Benzyl Ester | Isotianil | Visual Weed Control (%)—20 DAA DIGSA | |
|---|---|---|---|
| g ae/ha | g ai/ha | Obs | Exp |
| 8 | 0 | 20 | — |
| 16 | 0 | 30 | — |
| 32 | 0 | 40 | — |
| 0 | 100 | 0 | — |
| 0 | 200 | 0 | — |
| 8 | 100 | 30 | 20 |
| 16 | 100 | 55 | 30 |
| 32 | 100 | 60 | 40 |
| 8 | 200 | 35 | 20 |
| 16 | 200 | 60 | 30 |
| 32 | 200 | 50 | 40 |

| Compound A Benzyl Ester | Isotianil | Visual Weed Control (%)—21 DAA | | | | | | | |
|---|---|---|---|---|---|---|---|---|---|
| | | BRAPP | | DIGSA | | ECHCG | | ECHCO | | LEFCH | |
| g ae/ha | g ai/ha | Obs | Exp | Obs | Exp | Obs | Exp | Obs | Exp | Obs | Exp |
| 8 | 0 | 55 | — | 15 | — | 45 | — | 50 | — | 25 | — |
| 16 | 0 | 60 | — | 25 | — | 85 | — | 65 | — | 40 | — |
| 0 | 380 | 0 | — | 0 | — | 0 | — | 0 | — | 0 | — |
| 8 | 380 | 80 | 55 | 50 | 15 | 80 | 45 | 80 | 50 | 55 | 25 |
| 16 | 380 | 90 | 60 | 50 | 25 | 85 | 85 | 90 | 65 | 55 | 40 |

TABLE 10

Synergistic Activity of Foliar-Applied Compound A Benzyl Ester and Kasugamycin Compositions on Weed Control in a Rice Cropping System.

| Compound A Benzyl Ester | Kasugamycin | Visual Weed Control (%)—21 DAA | | | | | | | |
|---|---|---|---|---|---|---|---|---|---|
| | | DIGSA | | ECHOR | | LEFCH | | IPOHE | |
| g ae/ha | g ai/ha | Obs | Exp | Obs | Exp | Obs | Exp | Obs | Exp |
| 8 | 0 | 20 | — | 20 | — | 40 | — | 0 | — |
| 16 | 0 | 40 | — | 60 | — | 40 | — | 30 | — |
| 32 | 0 | 50 | — | 85 | — | 65 | — | 55 | — |
| 0 | 17.5 | 0 | — | 0 | — | 0 | — | 0 | — |
| 0 | 35 | 0 | — | 0 | — | 0 | — | 0 | — |
| 0 | 70 | 0 | — | 0 | — | 0 | — | 0 | — |
| 8 | 17.5 | 30 | 20 | 40 | 20 | 50 | 40 | 10 | 0 |
| 16 | 17.5 | 40 | 40 | 65 | 60 | 60 | 40 | 50 | 30 |

TABLE 10-continued

Synergistic Activity of Foliar-Applied Compound A Benzyl Ester and Kasugamycin Compositions on Weed Control in a Rice Cropping System.

| 32 | 17.5 | 55 | 50 | 90 | 85 | 75 | 65 | 65 | 55 |
|----|------|----|----|----|----|----|----|----|----|
| 8  | 35   | 25 | 20 | 60 | 20 | 50 | 40 | 25 | 0  |
| 16 | 35   | 40 | 40 | 80 | 60 | 70 | 40 | 50 | 30 |
| 32 | 35   | 65 | 50 | 95 | 85 | 65 | 65 | 65 | 55 |
| 8  | 70   | 40 | 20 | 35 | 20 | 45 | 40 | 50 | 0  |
| 16 | 70   | 45 | 40 | 65 | 60 | 55 | 40 | 45 | 30 |
| 32 | 70   | 60 | 50 | 95 | 85 | 70 | 65 | 70 | 55 |

| Compound A Benzyl Ester | Kasugamycin | Visual Weed Control (%)—21 DAA CYPIR | |
|---|---|---|---|
| g ae/ha | g ai/ha | Obs | Exp |
| 8  | 0    | 50  | — |
| 16 | 0    | 70  | — |
| 0  | 17.5 | 0   | — |
| 0  | 35   | 0   | — |
| 0  | 70   | 0   | — |
| 8  | 17.5 | 85  | 50 |
| 16 | 17.5 | 100 | 70 |
| 8  | 35   | 50  | 50 |
| 16 | 35   | 100 | 70 |
| 8  | 70   | 50  | 50 |
| 16 | 70   | 100 | 70 |

| Compound A Benzyl Ester | Kasugamycin | Visual Weed Control (%)—21 DAA CYPES | |
|---|---|---|---|
| g ae/ha | g ai/ha | Obs | Exp |
| 8  | 0    | 70 | — |
| 0  | 17.5 | 0  | — |
| 0  | 35   | 0  | — |
| 0  | 70   | 0  | — |
| 8  | 17.5 | 95 | 70 |
| 8  | 35   | 70 | 70 |
| 8  | 70   | 85 | 70 |

TABLE 11

Synergistic Activity of Foliar-Applied Compound A Benzyl Ester and Mancozeb Compositions on Weed Control in a Rice Cropping System.

| Compound A Benzyl Ester | Mancozeb | Visual Weed Control (%) - 21 DAA LEFCH | |
|---|---|---|---|
| g ae/ha | g ai/ha | Obs | Exp |
| 16 | 0   | 15 | — |
| 32 | 0   | 25 | — |
| 0  | 840 | 0  | — |
| 16 | 840 | 25 | 15 |
| 32 | 840 | 45 | 25 |

| Compound A Benzyl Ester | Mancozeb | Visual Weed Control (%) - 21 DAA IPOHE | |
|---|---|---|---|
| g ae/ha | g ai/ha | Obs | Exp |
| 8  | 0    | 10 | — |
| 16 | 0    | 50 | — |
| 32 | 0    | 60 | — |
| 0  | 1680 | 0  | — |
| 8  | 1680 | 20 | 10 |
| 16 | 1680 | 70 | 50 |
| 32 | 1680 | 70 | 60 |

TABLE 12

Synergistic Activity of Foliar-Applied Compound A Acid and Myclobutanil Compositions on Weed Control in a Rice Cropping System.

| Compound A Acid | Myclobutanil | Visual Weed Control (%) - 21 DAA | | | |
|---|---|---|---|---|---|
| | | LEFCH | | IPOHE | |
| g ae/ha | g ai/ha | Obs | Exp | Obs | Exp |
| 5.3  | 0   | 10 | —  | 10 | —  |
| 10.6 | 0   | 20 | —  | 15 | —  |
| 21.2 | 0   | 45 | —  | 20 | —  |
| 0    | 250 | 0  | —  | 10 | —  |
| 5.3  | 250 | 10 | 10 | 10 | 19 |
| 10.6 | 250 | 30 | 20 | 10 | 24 |
| 21.2 | 250 | 70 | 45 | 65 | 28 |

TABLE 13

Synergistic Activity of Foliar-Applied Compound A Benzyl Ester and Myclobutanil Compositions on Weed Control in a Rice Cropping System.

| Compound A Benzyl Ester | Myclobutanil | Visual Weed Control (%) - 21 DAA | | | |
|---|---|---|---|---|---|
| | | LEFCH | | IPOHE | |
| g ae/ha | g ai/ha | Obs | Exp | Obs | Exp |
| 4.38 | 0 | 10 | — | 10 | — |
| 8.75 | 0 | 20 | — | 10 | — |

TABLE 13-continued

Synergistic Activity of Foliar-Applied Compound A Benzyl Ester and Myclobutanil Compositions on Weed Control in a Rice Cropping System.

| 17.5 | 0 | 55 | — | 20 | — |
|---|---|---|---|---|---|
| 0 | 250 | 0 | — | 10 | — |
| 4.38 | 250 | 30 | 10 | 10 | 19 |
| 8.75 | 250 | 60 | 20 | 10 | 19 |
| 17.5 | 250 | 75 | 55 | 45 | 28 |

| Compound A Benzyl Ester | Myclobutanil | Visual Weed Control (%) - 21 DAA LEFCH | |
|---|---|---|---|
| g ae/ha | g ai/ha | Obs | Exp |
| 8 | 0 | 23 | — |
| 16 | 0 | 25 | — |
| 32 | 0 | 43 | — |
| 0 | 200 | 0 | — |
| 8 | 200 | 30 | 23 |
| 16 | 200 | 50 | 25 |
| 32 | 200 | 65 | 43 |

| Compound A Benzyl Ester | Myclobutanil | Visual Weed Control (%) - 21 DAA ECHCG | |
|---|---|---|---|
| g ae/ha | g ai/ha | Obs | Exp |
| 8 | 0 | 70 | — |
| 16 | 0 | 60 | — |
| 32 | 0 | 90 | — |
| 0 | 50 | 0 | — |
| 0 | 100 | 0 | — |
| 0 | 200 | 0 | — |
| 8 | 50 | 88 | 70 |
| 16 | 50 | 90 | 60 |
| 32 | 50 | 97 | 90 |
| 8 | 100 | 90 | 70 |
| 16 | 100 | 93 | 60 |
| 32 | 100 | 95 | 90 |
| 8 | 200 | 90 | 70 |
| 16 | 200 | 93 | 60 |
| 32 | 200 | 95 | 90 |

| Compound A Benzyl Ester | Myclobutanil | Visual Weed Control (%) - 21 DAA ECHOR | |
|---|---|---|---|
| g ae/ha | g ai/ha | Obs | Exp |
| 8 | 0 | 45 | — |
| 16 | 0 | 43 | — |
| 32 | 0 | 70 | — |
| 0 | 50 | 0 | — |
| 0 | 100 | 0 | — |
| 0 | 200 | 0 | — |
| 8 | 50 | 80 | 45 |
| 16 | 50 | 85 | 43 |
| 32 | 50 | 95 | 70 |
| 8 | 100 | 90 | 45 |
| 16 | 100 | 93 | 43 |
| 32 | 100 | 97 | 70 |
| 8 | 200 | 85 | 45 |
| 16 | 200 | 90 | 43 |
| 32 | 200 | 97 | 70 |

TABLE 14

Synergistic Activity of Foliar-Applied Compound A Benzyl Ester and Phthalide Compositions on Weed Control in a Rice Cropping System.

| Compound A Benzyl Ester | Phthalide | Visual Weed Control (%) - 21 DAA ECHCG | |
|---|---|---|---|
| g ae/ha | g ai/ha | Obs | Exp |
| 8 | 0 | 80 | — |
| 16 | 0 | 95 | — |
| 0 | 100 | 0 | — |
| 0 | 200 | 0 | — |
| 0 | 300 | 0 | — |
| 8 | 100 | 95 | 80 |
| 16 | 100 | 99 | 95 |
| 8 | 200 | 90 | 80 |
| 16 | 200 | 95 | 95 |
| 8 | 300 | 95 | 80 |
| 16 | 300 | 95 | 95 |

| Compound A Benzyl Ester | Phthalide | Visual Weed Control (%) - 21 DAA CYPES | |
|---|---|---|---|
| g ae/ha | g ai/ha | Obs | Exp |
| 8 | 0 | 10 | — |
| 0 | 100 | 0 | — |
| 0 | 200 | 0 | — |
| 0 | 300 | 10 | — |
| 8 | 100 | 60 | 10 |
| 8 | 200 | 30 | 10 |
| 8 | 300 | 85 | 19 |

TABLE 15

Synergistic Activity of Foliar-Applied Compound A Benzyl Ester and Probenazole Compositions on Weed Control in a Rice Cropping System.

| Compound A Benzyl Ester | Probenazole | Visual Weed Control (%)—19 DAA ECHCO | |
|---|---|---|---|
| g ae/ha | g ai/ha | Obs | Exp |
| 8 | 0 | 65 | — |
| 0 | 500 | 0 | — |
| 8 | 500 | 85 | 65 |

| Compound A Benzyl Ester | Probenazole | Visual Weed Control (%)—21 DAA CYPES | |
|---|---|---|---|
| g ae/ha | g ai/ha | Obs | Exp |
| 8 | 0 | 10 | — |
| 16 | 0 | 90 | — |

TABLE 15-continued

Synergistic Activity of Foliar-Applied Compound A Benzyl Ester and Probenazole Compositions on Weed Control in a Rice Cropping System.

| | | | |
|---|---|---|---|
| 0 | 1888 | 15 | — |
| 8 | 1888 | 70 | 24 |
| 16 | 1888 | 99 | 92 |

| Compound A Benzyl Ester | Probenazole | Visual Weed Control (%)—21 DAA | | | | | |
|---|---|---|---|---|---|---|---|
| | | ORYSA 'Clearfield 171' (2.5-leaf) | | ORYSA 'Clearfield 171' (1.5-leaf) | | ORYSA 'Wells' (2-leaf) | |
| g ae/ha | g ai/ha | Obs | Exp | Obs | Exp | Obs | Exp |
| 8 | 0 | 0 | — | 0 | — | 10 | — |
| 16 | 0 | 0 | — | 10 | — | 0 | — |
| 32 | 0 | 0 | — | 0 | — | 10 | — |
| 0 | 1888 | 0 | — | 10 | — | 0 | — |
| 8 | 1888 | 30 | 0 | 25 | 10 | 0 | 10 |
| 16 | 1888 | 20 | 0 | 25 | 19 | 30 | 0 |
| 32 | 1888 | 0 | 0 | 25 | 10 | 30 | 10 |

TABLE 16

Synergistic Activity of Foliar-Applied Compound A Acid and Propiconazole Compositions on Weed Control in a Rice Cropping System.

| Compound A Acid | Propiconazole | Visual Weed Control (%) - 21 DAA DIGSA | |
|---|---|---|---|
| g ae/ha | g ai/ha | Obs | Exp |
| 5.3 | 0 | 10 | — |
| 10.6 | 0 | 20 | — |
| 21.2 | 0 | 20 | — |
| 0 | 190 | 0 | — |
| 5.3 | 190 | 0 | 10 |
| 10.6 | 190 | 40 | 20 |
| 21.2 | 190 | 40 | 20 |

TABLE 17

Synergistic Activity of Foliar-Applied Compound A Benzyl Ester and Propiconazole Compositions on Weed Control in a Rice Cropping System.

| Compound A Benzyl Ester | Propiconazole | Visual Weed Control (%) - 20 DAA | | | |
|---|---|---|---|---|---|
| | | CYPES | | SCPJU | |
| g ae/ha | g ai/ha | Obs | Exp | Obs | Exp |
| 8 | 0 | 0 | — | 70 | — |
| 16 | 0 | 75 | — | 85 | — |
| 0 | 62.5 | 0 | — | 0 | — |
| 0 | 125 | 0 | — | 0 | — |
| 0 | 250 | 0 | — | 0 | — |
| 8 | 62.5 | 63 | 0 | 70 | 70 |
| 16 | 62.5 | 85 | 75 | 95 | 85 |
| 8 | 125 | 80 | 0 | 95 | 70 |
| 16 | 125 | 80 | 75 | 100 | 85 |
| 8 | 250 | 73 | 0 | 90 | 70 |
| 16 | 250 | 93 | 75 | 99 | 85 |

TABLE 18

Synergistic Activity of Foliar-Applied Compound A Benzyl Ester and Pyroquilon Compositions on Weed Control in a Rice Cropping System.

| Compound A Benzyl Ester | Pyroquilon | Visual Weed Control (%) - 21 DAA CYPES | |
|---|---|---|---|
| g ae/ha | g ai/ha | Obs | Exp |
| 8 | 0 | 10 | — |
| 16 | 0 | 90 | — |
| 0 | 925 | 0 | — |
| 8 | 925 | 85 | 10 |
| 16 | 925 | 100 | 90 |

| Compound A Benzyl Ester | Pyroquilon | Visual Weed Control (%) - 21 DAA CYPIR | |
|---|---|---|---|
| g ae/ha | g ai/ha | Obs | Exp |
| 16 | 0 | 85 | — |
| 32 | 0 | 99 | — |
| 0 | 925 | 0 | — |
| 16 | 925 | 99 | 85 |
| 32 | 925 | 100 | 99 |

TABLE 19

Synergistic Activity of Foliar-Applied Compound A Acid and Tebuconazole Compositions on Weed Control in a Rice Cropping System.

| Compound A Acid | Tebuconazole | Visual Weed Control (%)—21 DAA | | | | | | | |
|---|---|---|---|---|---|---|---|---|---|
| | | DIGSA | | ECHCG | | LEFCH | | IPOHE | |
| g ae/ha | g ai/ha | Obs | Exp | Obs | Exp | Obs | Exp | Obs | Exp |
| 5.3 | 0 | 10 | — | 80 | — | 10 | — | 10 | — |
| 10.6 | 0 | 20 | — | 90 | — | 20 | — | 15 | — |
| 21.2 | 0 | 20 | — | 95 | — | 45 | — | 20 | — |
| 0 | 250 | 0 | — | 0 | — | 0 | — | 0 | — |
| 5.3 | 250 | 25 | 10 | 95 | 80 | 10 | 10 | 15 | 10 |
| 10.6 | 250 | 40 | 20 | 95 | 90 | 50 | 20 | 15 | 15 |
| 21.2 | 250 | 60 | 20 | 99 | 95 | 85 | 45 | 60 | 20 |

TABLE 20

Synergistic Activity of Foliar-Applied Compound A Benzyl Ester and Tebuconazole Compositions on Weed Control in a Rice Cropping System.

| Compound A Benzyl Ester | Tebuconazole | Visual Weed Control (%) - 21 DAA LEFCH | |
|---|---|---|---|
| g ae/ha | g ai/ha | Obs | Exp |
| 4.38 | 0 | 10 | — |
| 8.75 | 0 | 20 | — |
| 17.5 | 0 | 55 | — |
| 0 | 250 | 0 | — |
| 4.38 | 250 | 20 | 10 |
| 8.75 | 250 | 60 | 20 |
| 17.5 | 250 | 65 | 55 |
| 8 | 0 | 23 | — |
| 16 | 0 | 25 | — |
| 32 | 0 | 43 | — |
| 0 | 62.5 | 5 | — |
| 0 | 125 | 10 | — |
| 0 | 250 | 8 | — |
| 8 | 62.5 | 55 | 26 |
| 16 | 62.5 | 53 | 29 |
| 32 | 62.5 | 75 | 45 |
| 8 | 125 | 50 | 30 |
| 16 | 125 | 58 | 33 |
| 32 | 125 | 70 | 48 |
| 8 | 250 | 43 | 28 |
| 16 | 250 | 60 | 31 |
| 32 | 250 | 80 | 47 |

| Compound A Benzyl Ester | Tebuconazole | Visual Weed Control (%) - 22 DAA BRAPP | |
|---|---|---|---|
| g ae/ha | g ai/ha | Obs | Exp |
| 8 | 0 | 65 | — |
| 0 | 62.5 | 0 | — |
| 0 | 125 | 0 | — |
| 0 | 250 | 0 | — |
| 8 | 62.5 | 78 | 65 |
| 8 | 125 | 63 | 65 |
| 8 | 250 | 85 | 65 |

| Compound A Benzyl Ester | Tebuconazole | Visual Weed Control (%) - 22 DAA CYPIR | |
|---|---|---|---|
| g ae/ha | g ai/ha | Obs | Exp |
| 8 | 0 | 75 | — |
| 16 | 0 | 73 | — |
| 32 | 0 | 60 | — |
| 0 | 125 | 0 | — |
| 0 | 250 | 0 | — |
| 8 | 125 | 68 | 75 |
| 16 | 125 | 90 | 73 |
| 32 | 125 | 100 | 60 |
| 8 | 250 | 100 | 75 |
| 16 | 250 | 100 | 73 |
| 32 | 250 | 100 | 60 |

| Compound A Benzyl Ester | Tebuconazole | Visual Weed Control (%) - 22 DAA IPOHE | |
|---|---|---|---|
| g ae/ha | g ai/ha | Obs | Exp |
| 8 | 0 | 15 | — |
| 16 | 0 | 33 | — |
| 0 | 62.5 | 0 | — |
| 8 | 62.5 | 30 | 15 |
| 16 | 62.5 | 53 | 33 |

| Compound A Benzyl Ester | Tebuconazole | Visual Weed Control (%) - 21 DAA ECHCG | |
|---|---|---|---|
| g ae/ha | g ai/ha | Obs | Exp |
| 8 | 0 | 70 | — |
| 16 | 0 | 60 | — |
| 32 | 0 | 90 | — |
| 0 | 62.5 | 0 | — |
| 0 | 125 | 5 | — |
| 0 | 250 | 8 | — |
| 8 | 62.5 | 90 | 70 |
| 16 | 62.5 | 95 | 60 |
| 32 | 62.5 | 95 | 90 |
| 8 | 125 | 88 | 72 |
| 16 | 125 | 90 | 62 |
| 32 | 125 | 95 | 91 |
| 8 | 250 | 93 | 72 |
| 16 | 250 | 90 | 63 |
| 32 | 250 | 97 | 91 |

| Compound A Benzyl Ester | Tebuconazole | Visual Weed Control (%) - 21 DAA ECHOR | |
|---|---|---|---|
| g ae/ha | g ai/ha | Obs | Exp |
| 8 | 0 | 45 | — |
| 16 | 0 | 43 | — |
| 32 | 0 | 70 | — |

TABLE 20-continued

Synergistic Activity of Foliar-Applied Compound A Benzyl Ester and Tebuconazole Compositions on Weed Control in a Rice Cropping System.

| 0 | 62.5 | 0 | — |
| 0 | 125 | 5 | — |
| 0 | 250 | 8 | — |
| 8 | 62.5 | 90 | 45 |
| 16 | 62.5 | 90 | 43 |
| 32 | 62.5 | 97 | 70 |
| 8 | 125 | 93 | 48 |
| 16 | 125 | 95 | 45 |
| 32 | 125 | 95 | 72 |
| 8 | 250 | 88 | 49 |
| 16 | 250 | 95 | 47 |
| 32 | 250 | 95 | 72 |

| Compound A Benzyl Ester | Tebuconazole | Visual Weed Control (%) - 22 DAA DIGSA | |
|---|---|---|---|
| g ae/ha | g ai/ha | Obs | Exp |
| 8 | 0 | 15 | — |
| 16 | 0 | 23 | — |
| 32 | 0 | 28 | — |
| 0 | 62.5 | 0 | — |
| 0 | 125 | 0 | — |
| 0 | 250 | 0 | — |
| 8 | 62.5 | 38 | 15 |
| 16 | 62.5 | 53 | 23 |
| 32 | 62.5 | 60 | 28 |
| 8 | 125 | 43 | 15 |
| 16 | 125 | 40 | 23 |
| 32 | 125 | 58 | 28 |
| 8 | 250 | 45 | 15 |
| 16 | 250 | 45 | 23 |
| 32 | 250 | 63 | 28 |

TABLE 21

Synergistic Activity of Foliar-Applied Compound A Benzyl Ester and Thifluzamide Compositions on Weed Control in a Rice Cropping System.

| Compound A Benzyl Ester | Thifluzamide | Visual Weed Control (%) - 20 DAA | | | |
|---|---|---|---|---|---|
| | | BRAPP | | DIGSA | |
| g ae/ha | g ai/ha | Obs | Exp | Obs | Exp |
| 8 | 0 | 60 | — | 20 | — |
| 16 | 0 | 85 | — | 30 | — |
| 32 | 0 | 90 | — | 40 | — |
| 0 | 75 | 0 | — | 0 | — |
| 0 | 150 | 0 | — | 0 | — |
| 0 | 300 | 0 | — | 0 | — |
| 8 | 75 | 80 | 60 | 30 | 20 |
| 16 | 75 | 75 | 85 | 45 | 30 |
| 32 | 75 | 95 | 90 | 45 | 40 |
| 8 | 150 | 80 | 60 | 50 | 20 |
| 16 | 150 | 95 | 85 | 40 | 30 |
| 32 | 150 | 95 | 90 | 50 | 40 |
| 8 | 300 | 80 | 60 | 35 | 20 |
| 16 | 300 | 85 | 85 | 30 | 30 |
| 32 | 300 | 95 | 90 | 35 | 40 |

TABLE 22

Synergistic Activity of Foliar-Applied Compound A Acid and Tricyclazole Compositions on Weed Control in a Rice Cropping System.

| Compound A Acid | Tricyclazole | Visual Weed Control (%) - 21 DAA IPOHE | |
|---|---|---|---|
| g ae/ha | g ai/ha | Obs | Exp |
| 5.3 | 0 | 10 | — |
| 10.6 | 0 | 15 | — |
| 21.2 | 0 | 20 | — |
| 0 | 200 | 0 | — |
| 5.3 | 200 | 30 | 10 |
| 10.6 | 200 | 25 | 15 |
| 21.2 | 200 | 60 | 20 |

TABLE 23

Synergistic Activity of Foliar-Applied Compound A Benzyl Ester and Tricyclazole Compositions on Weed Control in a Rice Cropping System.

| Compound A Benzyl Ester | Tricyclazole | Visual Weed Control (%) - 21 DAA IPOHE | |
|---|---|---|---|
| g ae/ha | g ai/ha | Obs | Exp |
| 4.38 | 0 | 10 | — |
| 8.75 | 0 | 10 | — |
| 17.5 | 0 | 20 | — |
| 0 | 200 | 0 | — |
| 4.38 | 200 | 15 | 10 |
| 8.75 | 200 | 15 | 10 |
| 17.5 | 200 | 40 | 20 |

| Compound A Benzyl Ester | Tricyclazole | Visual Weed Control (%) - 21 DAA ECHCG | |
|---|---|---|---|
| g ae/ha | g ai/ha | Obs | Exp |
| 8 | 0 | 70 | — |
| 16 | 0 | 60 | — |
| 32 | 0 | 90 | — |
| 0 | 50 | 0 | — |
| 0 | 100 | 0 | — |
| 0 | 200 | 0 | — |
| 8 | 50 | 75 | 70 |
| 16 | 50 | 80 | 60 |
| 32 | 50 | 95 | 90 |
| 8 | 100 | 65 | 70 |
| 16 | 100 | 78 | 60 |
| 32 | 100 | 93 | 90 |
| 8 | 200 | 85 | 70 |
| 16 | 200 | 90 | 60 |
| 32 | 200 | 95 | 90 |

| Compound A Benzyl Ester | Tricyclazole | Visual Weed Control (%) - 21 DAA ECHOR | |
|---|---|---|---|
| g ae/ha | g ai/ha | Obs | Exp |
| 8 | 0 | 45 | — |
| 16 | 0 | 43 | — |
| 32 | 0 | 70 | — |
| 0 | 50 | 0 | — |
| 0 | 100 | 0 | — |
| 0 | 200 | 0 | — |
| 8 | 50 | 58 | 45 |

TABLE 23-continued

Synergistic Activity of Foliar-Applied Compound A Benzyl Ester and Tricyclazole Compositions on Weed Control in a Rice Cropping System.

| 16 | 50  | 68 | 43 |
| 32 | 50  | 90 | 70 |
| 8  | 100 | 48 | 45 |
| 16 | 100 | 55 | 43 |
| 32 | 100 | 93 | 70 |
| 8  | 200 | 58 | 45 |
| 16 | 200 | 78 | 43 |
| 32 | 200 | 90 | 70 |

| Compound A Benzyl Ester | Tricyclazole | Visual Weed Control (%) - 22 DAA IPOHE | |
|---|---|---|---|
| g ae/ha | g ai/ha | Obs | Exp |
| 8  | 0   | 15 | — |
| 16 | 0   | 33 | — |
| 0  | 50  | 0  | — |
| 0  | 100 | 0  | — |
| 0  | 200 | 10 | — |
| 8  | 50  | 28 | 15 |
| 16 | 50  | 55 | 33 |
| 8  | 100 | 15 | 15 |
| 16 | 100 | 55 | 33 |
| 8  | 200 | 38 | 24 |
| 16 | 200 | 45 | 39 |

TABLE 24

Synergistic Activity of Foliar-Applied Compound A Benzyl Ester and Trifloxystrobin Compositions on Weed Control in a Rice Cropping System.

| Compound A Benzyl Ester | Trifloxystrobin | Visual Weed Control (%) - 21 DAA CYPIR | |
|---|---|---|---|
| g ae/ha | g ai/ha | Obs | Exp |
| 8  | 0   | 50  | — |
| 16 | 0   | 70  | — |
| 32 | 0   | 100 | — |
| 0  | 140 | 0   | — |
| 8  | 140 | 70  | 50 |
| 16 | 140 | 95  | 70 |
| 32 | 140 | 100 | 100 |

| Compound A Benzyl Ester | Trifloxystrobin | Visual Weed Control (%) - 20 DAA DIGSA | |
|---|---|---|---|
| g ae/ha | g ai/ha | Obs | Exp |
| 8 | 0   | 15 | — |
| 0 | 75  | 0  | — |
| 0 | 150 | 0  | — |
| 0 | 300 | 0  | — |
| 8 | 75  | 30 | 15 |
| 8 | 150 | 10 | 15 |
| 8 | 300 | 30 | 15 |

| Compound A Benzyl Ester | Trifloxystrobin | Visual Weed Control (%) - 20 DAA CYPES | |
|---|---|---|---|
| g ae/ha | g ai/ha | Obs | Exp |
| 16 | 0  | 40 | — |
| 0  | 75 | 0  | — |

TABLE 24-continued

Synergistic Activity of Foliar-Applied Compound A Benzyl Ester and Trifloxystrobin Compositions on Weed Control in a Rice Cropping System.

| 0  | 150 | 0  | — |
| 16 | 75  | 70 | 40 |
| 16 | 150 | 60 | 40 |

TABLE 25

Synergistic Activity of Foliar-Applied Compound A Benzyl Ester and a Compound of Formula (II) Compositions on Weed Control in a Rice Cropping System.

| Compound A Benzyl Ester | Compound of Formula (II) | Visual Weed Control (%) - 21 DAA BRAPP | |
|---|---|---|---|
| g ae/ha | g ai/ha | Obs | Exp |
| 8 | 0    | 70 | — |
| 0 | 37.5 | 0  | — |
| 0 | 75   | 0  | — |
| 0 | 150  | 0  | — |
| 8 | 37.5 | 80 | 70 |
| 8 | 75   | 90 | 70 |
| 8 | 150  | 90 | 70 |

| Compound A Benzyl Ester | Compound of Formula (II) | Visual Weed Control (%) - 21 DAA ECHCG | |
|---|---|---|---|
| g ae/ha | g ai/ha | Obs | Exp |
| 16 | 0   | 80 | — |
| 32 | 0   | 95 | — |
| 0  | 150 | 0  | — |
| 16 | 150 | 95 | 80 |
| 32 | 150 | 99 | 95 |

| Compound A Benzyl Ester | Compound of Formula (II) | Visual Weed Control (%) - 21 DAA LEFCH | |
|---|---|---|---|
| g ae/ha | g ai/ha | Obs | Exp |
| 32 | 0    | 25 | — |
| 0  | 37.5 | 0  | — |
| 0  | 75   | 0  | — |
| 0  | 150  | 0  | — |
| 32 | 37.5 | 40 | 25 |
| 32 | 75   | 50 | 25 |
| 32 | 150  | 30 | 25 |

| Compound A Benzyl Ester | Compound of Formula (II) | Visual Weed Control (%) - 21 DAA CYPIR | |
|---|---|---|---|
| g ae/ha | g ai/ha | Obs | Exp |
| 8 | 0    | 50 | |
| 0 | 37.5 | 0  | |
| 0 | 75   | 0  | |

TABLE 25-continued

Synergistic Activity of Foliar-Applied Compound A
Benzyl Ester and a Compound of Formula (II)
Compositions on Weed Control in a Rice Cropping System.

| 8 | 37.5 | 70 | 50 |
| 8 | 75 | 100 | 50 |

BRAPP *Brachiaria platyphylla* (Groseb.) Nash; broadleaf signalgrass
CYPES *Cyperus esculentus* L.; nutsedge, yellow
CYPIR *Cyperus iria* L.; flatsedge, rice
DIGSA *Digitaria sanguinalis* (L.) Scop.; crabgrass, large
ECHCG *Echinochloa crus-galli* (L.) Beauv.; barnyardgrass
ECHCO *Echinochloa colonum* (L.) Link; junglerice
ECHOR *Echinochloa oryzoides* (Ard.) Fritsch; early watergrass
IPOHE *Ipomoea hederacea* Jacq.; morningglory, ivyleaf
LEFCH *Leptochloa chinensis* (L.) Nees; sprangletop, Chinese
ORYSA *Oryza sativa* L.; rice
SCPJU *Schoenoplectus juncoides* Roxb.; bulrush, Japanese
g ae/ha = grams acid equivalent per hectare
g ai/ha = grams active ingredient per hectare
Obs = observed value
Exp = expected value as calculated by Colby's equation
DAA = days after application Example II Evaluation of In-Water Applied Herbicidal Mixtures for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters (cm$^2$) leaving a headspace of 3 centimeters (cm) in each pot. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 860 mL of mud contained in 32-oz. non-perforated plastic pots with a surface area of 86.59 cm$^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 hour (h) photoperiod which was maintained at about 29° C. during the day and about 26° C. during the night. Nutrients were added as Osmocote® (17:6:10, N:P:K+minor nutrients) at 2 g per cup. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (compound A) each formulated as an SC (suspension concentrate) and various fungicidal components alone and in combination. Forms of compound A were applied on an acid equivalent basis.

Forms of compound A (compound of formula I) tested include:

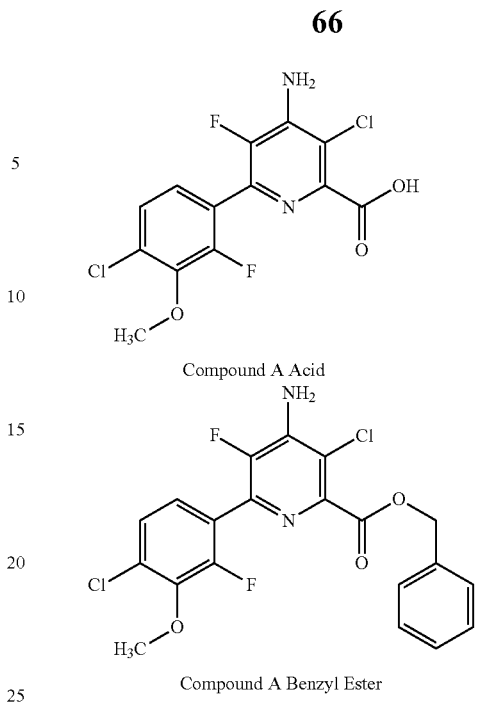

Compound A Acid

Compound A Benzyl Ester

Other fungicidal components were applied on an active ingredient basis and consisted of flutolanil (technical grade material), isoprothiolane (technical grade material), phthalide (technical grade materials), probenazole (technical grade material), and tricyclazole formulated as Beam®.

Treatment requirements for each compound or fungicidal component were calculated based upon the rates being tested, the concentration of active ingredient or acid equivalent in the formulation, an application volume of 2 mL per component per pot, and an application area of 86.59 cm$^2$ per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount was placed in an individual 100 to 200 mL glass vial and dissolved in a volume of acetone to obtain concentrated stock solutions. If the test compound did not dissolve readily, the mixture was warmed and/or sonicated. The concentrated stock solutions obtained were diluted with an equivalent volume of an aqueous mixture containing 2.5% (v/v) crop oil concentrate so that the final application solutions contained 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture;

B=observed efficacy of active ingredient B at the same concentration as used in the mixture.

Some of the compounds tested, application rates employed, plant species tested, and results are given in Tables 26-31.

TABLE 26

Synergistic Activity of In-Water Applied Compound A Benzyl Ester and Flutolanil Compositions on Weed Control in a Transplanted Rice Cropping System.

| Compound A Benzyl Ester | Flutolanil | Visual Weed Control (%) - 21 DAA ECHOR | |
|---|---|---|---|
| g ae/ha | g ai/ha | Obs | Exp |
| 8 | 0 | 15 | — |
| 16 | 0 | 20 | — |
| 0 | 140 | 0 | — |
| 0 | 560 | 0 | — |
| 8 | 140 | 45 | 15 |
| 16 | 140 | 75 | 20 |
| 8 | 560 | 30 | 15 |
| 16 | 560 | 50 | 20 |

| Compound A Benzyl Ester | Flutolanil | Visual Weed Control (%) - 21 DAA LEFCH | |
|---|---|---|---|
| g ae/ha | g ai/ha | Obs | Exp |
| 8 | 0 | 0 | — |
| 16 | 0 | 0 | — |
| 0 | 140 | 0 | — |
| 8 | 140 | 20 | 0 |
| 16 | 140 | 20 | 0 |

TABLE 27

Synergistic Activity of In-Water Applied Compound A Benzyl Ester and Isoprothiolane Compositions on Weed Control in a Transplanted Rice Cropping System.

| Compound A Benzyl Ester | Isoprothiolane | Visual Weed Control (%) - 22 DAA ECHOR | |
|---|---|---|---|
| g ae/ha | g ai/ha | Obs | Exp |
| 8 | 0 | 55 | — |
| 16 | 0 | 83 | — |
| 32 | 0 | 95 | — |
| 0 | 200 | 0 | — |
| 0 | 300 | 0 | — |
| 8 | 200 | 73 | 55 |
| 16 | 200 | 90 | 83 |
| 32 | 200 | 97 | 95 |
| 8 | 300 | 50 | 55 |
| 16 | 300 | 80 | 83 |
| 32 | 300 | 97 | 95 |

| Compound A Benzyl Ester | Isoprothiolane | Visual Weed Control (%) - 22 DAA LEFCH | |
|---|---|---|---|
| g ae/ha | g ai/ha | Obs | Exp |
| 8 | 0 | 85 | — |
| 16 | 0 | 90 | — |
| 32 | 0 | 100 | — |
| 0 | 200 | 0 | — |
| 8 | 200 | 100 | 85 |
| 16 | 200 | 100 | 90 |
| 32 | 200 | 98 | 100 |

TABLE 28

Synergistic Activity of In-Water Applied Compound A Benzyl Ester and Phthalide Compositions on Weed Control in a Transplanted Rice Cropping System.

| Compound A Benzyl Ester | Phthalide | Visual Weed Control (%) - 22 DAA ECHOR | |
|---|---|---|---|
| g ae/ha | g ai/ha | Obs | Exp |
| 8 | 0 | 55 | — |
| 16 | 0 | 83 | — |
| 32 | 0 | 95 | — |
| 0 | 100 | 0 | — |
| 0 | 200 | 0 | — |
| 0 | 300 | 0 | — |
| 8 | 100 | 73 | 55 |
| 16 | 100 | 90 | 83 |
| 32 | 100 | 98 | 95 |
| 8 | 200 | 65 | 55 |
| 16 | 200 | 78 | 83 |
| 32 | 200 | 99 | 95 |
| 8 | 300 | 68 | 55 |
| 16 | 300 | 80 | 83 |
| 32 | 300 | 97 | 95 |

| Compound A Benzyl Ester | Phthalide | Visual Weed Control (%) - 22 DAA LEFCH | |
|---|---|---|---|
| g ae/ha | g ai/ha | Obs | Exp |
| 8 | 0 | 85 | — |
| 16 | 0 | 90 | — |
| 0 | 100 | 0 | — |
| 0 | 300 | 0 | — |
| 8 | 100 | 95 | 85 |
| 16 | 100 | 100 | 90 |
| 8 | 300 | 100 | 85 |
| 16 | 300 | 100 | 90 |

TABLE 29

Synergistic Activity of In-Water Applied Compound A Benzyl Ester and Probenazole Compositions on Weed Control in a Transplanted Rice Cropping System.

| Compound A Benzyl Ester | Probenazole | Visual Weed Control (%) - 21 DAA CYPRO | |
|---|---|---|---|
| g ae/ha | g ai/ha | Obs | Exp |
| 8 | 0 | 40 | — |
| 0 | 1000 | 0 | — |
| 0 | 2000 | 0 | — |
| 0 | 4000 | 0 | — |
| 8 | 1000 | 95 | 40 |
| 8 | 2000 | 80 | 40 |
| 8 | 4000 | 75 | 40 |

| Compound A Benzyl Ester | Probenazole | Visual Weed Control (%) - 21 DAA FIMMI | |
|---|---|---|---|
| g ae/ha | g ai/ha | Obs | Exp |
| 8 | 0 | 40 | — |
| 16 | 0 | 60 | — |
| 32 | 0 | 85 | — |
| 0 | 1000 | 0 | — |
| 0 | 2920 | 0 | — |
| 8 | 1000 | 5 | 40 |
| 16 | 1000 | 43 | 60 |
| 32 | 1000 | 100 | 85 |
| 8 | 2920 | 48 | 40 |
| 16 | 2920 | 90 | 60 |
| 32 | 2920 | 100 | 85 |

TABLE 30

Synergistic Activity of In-Water Applied Compound A Acid and Tricyclazole Compositions on Weed Control in a Transplanted Rice Cropping System.

| Compound A Acid | Tricyclazole | Visual Weed Control (%) - 22 DAA CYPRO | |
|---|---|---|---|
| g ae/ha | g ai/ha | Obs | Exp |
| 10.6 | 0 | 0 | — |
| 21.2 | 0 | 25 | — |
| 42.4 | 0 | 95 | — |
| 0 | 200 | 0 | — |
| 10.6 | 200 | 80 | 0 |
| 21.2 | 200 | 70 | 25 |
| 42.4 | 200 | 90 | 95 |

TABLE 31

Synergistic Activity of In-Water Applied Compound A Benzyl Ester and Tricyclazole Compositions on Weed Control in a Transplanted Rice Cropping System.

| Compound A Benzyl Ester | Tricyclazole | Visual Weed Control (%) - 19 DAA CYPRO | |
|---|---|---|---|
| g ae/ha | g ai/ha | Obs | Exp |
| 8 | 0 | 20 | — |
| 16 | 0 | 88 | — |
| 32 | 0 | 87 | — |
| 0 | 375 | 0 | — |
| 0 | 750 | 0 | — |
| 8 | 375 | 10 | 20 |
| 16 | 375 | 83 | 88 |
| 32 | 375 | 98 | 87 |
| 8 | 750 | 50 | 20 |
| 16 | 750 | 80 | 88 |
| 32 | 750 | 88 | 87 |

| Compound A Benzyl Ester | Tricyclazole | Visual Weed Control (%) - 22 DAA FIMMI | |
|---|---|---|---|
| g ae/ha | g ai/ha | Obs | Exp |
| 4.38 | 0 | 50 | — |
| 8.75 | 0 | 80 | — |
| 17.5 | 0 | 100 | — |
| 0 | 200 | 0 | — |
| 4.38 | 200 | 100 | 50 |
| 8.75 | 200 | 100 | 80 |
| 17.5 | 200 | 100 | 100 |

| Compound A Benzyl Ester | Tricyclazole | Visual Weed Control (%) - 19 DAA LEFCH | |
|---|---|---|---|
| g ae/ha | g ai/ha | Obs | Exp |
| 8 | 0 | 3 | — |
| 16 | 0 | 8 | — |
| 0 | 187.5 | 0 | — |
| 0 | 750 | 0 | — |
| 8 | 187.5 | 3 | 3 |
| 16 | 187.5 | 20 | 8 |
| 8 | 750 | 17 | 3 |
| 16 | 750 | 13 | 8 |

CYPRO *Cyperus rotundus* L.; nutsedge, purple
ECHCO *Echinochloa colonum* (L.) Link; junglerice
ECHOR *Echinochloa oryzoides* (Ard.) Fritsch; early watergrass
FIMMI *Fimbristylis miliacea* (L.) Vahl; globe fringerush
LEFCH *Leptochloa chinensis* (L.) Nees; sprangletop, Chinese
g ae/ha = grams acid equivalent per hectare
g ai/ha = grams active ingredient per hectare
Obs = observed value
Exp = expected value as calculated by Colby's equation
DAA = days after application

What is claimed is:
1. A herbicidal composition comprising a herbicidally effective amount of (a) a compound of the formula (I):

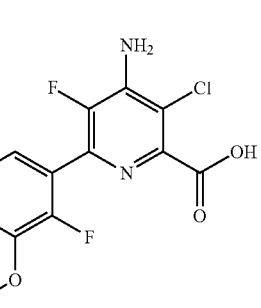

(I)

or an alkyl or benzyl ester, or an agriculturally acceptable salt of formula (I) and (b) a compound selected from the group consisting of: azoxystrobin, carbendazim, difenoconazole, flutolanil, hexaconazole, isoprothiolane, isotianil, kasugamycin, mancozeb, myclobutanil, phthalide, probenazole, propiconazole, pyroquilon, tebuconazole, thifluzamide, tricyclazole, trifloxystrobin, and a compound of formula (II):

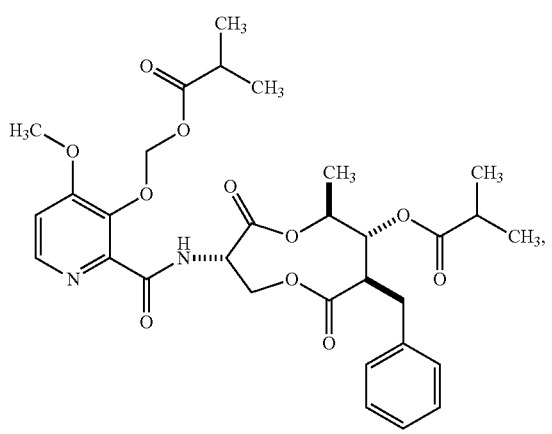

wherein (a) and (b) are present in the composition in a ratio such that the composition exhibits herbicidal synergy, wherein a weight ratio of the compound of formula (I) or an alkyl or benzyl ester, or an agriculturally acceptable salt of formula (I) to azoxystrobin is from about 1:500 to about 12:1, the weight ratio of the compound of formula (I) or an alkyl or benzyl ester, or an agriculturally acceptable salt of formula (I) to carbendazim is from about 1:375 to about 12:1 the weight ratio of the compound of formula (I) or an alkyl or benzyl ester, or an agriculturally acceptable salt of formula (I) to difenoconazole is from about 1:250 to about 12:1, the weight ratio of the compound of formula (I) or an alkyl or benzyl ester, or an agriculturally acceptable salt of formula (I) to flutolanil is from about 1:500 to about 12:1, the weight ratio of the compound of formula (I) or an alkyl or benzyl ester, or an agriculturally acceptable salt of formula (I) to hexaconazole is from about 1:250 to about 60:1, the weight ratio of the compound of formula (I) or an alkyl or benzyl ester, or an agriculturally acceptable salt of formula (I) to isoprothiolane is from about 1:500 to about 6:1, the weight ratio of the compound of formula (I) or an alkyl or benzyl ester, or an agriculturally acceptable salt of formula (I) to isotianil is from about 1:500 to about 30:1, the weight ratio of the compound of formula (I) or an alkyl or benzyl ester, or an agriculturally acceptable salt of formula (I) to kasugamycin is from about 1:250 to about 150:1, the weight ratio of the compound of formula (I) or an alkyl or benzyl ester, or an agriculturally acceptable salt of formula (I) to mancozeb is from about 1:2500 to about 12:1, the weight ratio of the compound of formula (I) or an alkyl or benzyl ester, or an agriculturally acceptable salt of formula (I) to myclobutanil is from about 1:250 to about 12:1, the weight ratio of the compound of formula (I) or an alkyl or benzyl ester, or an agriculturally acceptable salt of formula (I) to phthalide is from about 1:500 to about 15:1, the weight ratio of the compound of formula (I) or an alkyl or benzyl ester, or an agriculturally acceptable salt of formula (I) to probenazole is from about 1:2500 to about 6:1, the weight ratio of the compound of formula (I) or an alkyl or benzyl ester, or an agriculturally acceptable salt of formula (I) to propiconazole is from about 1:250 to about 30:1, the weight ratio of the compound of formula (I) or an alkyl or benzyl ester, or an agriculturally acceptable salt of formula (I) to pyroquilon is from about 1:1500 to about 3:1, the weight ratio of the compound of formula (I) or an alkyl or benzyl ester, or an agriculturally acceptable salt of formula (I) to tebuconazole is from about 1:250 to about 12:1, the weight ratio of the compound of formula (I) or an alkyl or benzyl ester, or an agriculturally acceptable salt of formula (I) to thifluzamide is from about 1:375 to about 30:1, the weight ratio of the compound of formula (I) or an alkyl or benzyl ester, or an agriculturally acceptable salt of formula (I) to tricyclazole is from about 1:500 to about 15:1, the weight ratio of the compound of formula (I) or an alkyl or benzyl ester, or an agriculturally acceptable salt of formula (I) to trifloxystrobin is from about 1:250 to about 30:1, or the weight ratio of compound of formula (I) or an alkyl or benzyl ester, or an agriculturally acceptable salt of formula (I) to a compound of formula (II) is from about 1:375 to about 150:1.

2. The composition of claim 1, wherein (a) is a benzyl ester of the compound of formula (I).

3. The composition of claim 1, wherein (a) is a $C_1$-$C_4$ alkyl ester of the compound of formula (I).

4. The composition of claim 1, wherein (a) is the compound of formula (I).

5. The composition of claim 1, further comprising at least one compound selected from the group consisting of: herbicide safeners, carriers and adjuvants.

6. The composition of claim 1, wherein (b) is selected from the group consisting of isoprothiolane, phthalide, and pyroquilon.

7. The composition of claim 1, wherein the ratio between the compound of the formula (I) and azoxystrobin is from about 1:11.8 to about 1:47.2; the ratio between the benzyl ester of the compound of formula (I) and azoxystrobin is from about 1:1.95 to about 1:57.1; wherein the ratio between the benzyl ester of the compound of formula (I) and carbendazim is from about 1:3.9 to about 1:31.3; wherein the ratio between the compound of the formula (I) and difenoconazole is from about 1:9.4 to about 1:37.7; wherein the ratio between the benzyl ester of the compound of formula (I) and difenoconazole is from about 1:1.6 to about 1:45.7; wherein the ratio between the benzyl ester of the compound of formula (I) and flutolanil is from about 1:8.8 to about 1:70; wherein the ratio between the benzyl ester of the compound of formula (I) and hexaconazole is from about 1.3:1 to about 1:12.5; wherein the ratio between the benzyl ester of the compound of formula (I) and isoprothiolane is from about 1:6.3 to about 1:66.6; wherein the ratio between the benzyl ester of the compound of formula (I) and isotianil is from about 1:3.1 to about 1:47.5; wherein the ratio between the benzyl ester of the compound of formula (I) and kasugamycin is from about 1.8:1 to about 1:8.8; wherein the ratio between the benzyl ester of the compound of formula (I) and mancozeb is from about 1:26.3 to about 1:210; wherein the ratio between the compound of the formula (I) and myclobutanil is from about 1:11.8 to about 1:23.6; wherein the ratio between the benzyl ester of the compound of formula (I) and myclobutanil is from about 1:1.6 to about 1:57.1; wherein the ratio between the benzyl ester of the compound of formula (I) and phthalide is from about 1:6.3 to about 1:37.5; wherein the ratio between the benzyl ester of the compound of formula (I) and probenazole is from about 1:31.3 to about 1:500; wherein the ratio between the compound of the formula (I) and propiconazole is from about 1:9 to about 1:35.9; wherein the ratio between the benzyl ester of the compound of formula (I) and propiconazole is from about 1:4 to about 1:31.3; wherein the ratio between the benzyl ester of the compound of formula (I) and pyroquilon is from about 1:28.9 to about 1:115.6; wherein the ratio between the compound of the formula (I) and tebuconazole is from about 1:11.8 to about 1:47.2; wherein the ratio between the benzyl ester of the compound of formula (I) and tebuconazole is from about 1:2.0 to about 1:57.1; wherein the ratio between the benzyl ester of the compound of formula (I) and thifluzamide is from about 1:2.3 to about 1:9.4; wherein the ratio between the compound of the formula (I) and tricyclazole is from about 1:9.4 to about 1:37.7; wherein the ratio between the benzyl ester of the compound of formula (I) and tricyclazole is from about 1:1.6 to about 1:93.8; wherein the ratio between the benzyl ester of the compound of formula (I) and trifloxystrobin is from about 1:8.8 to about 1:37.5; wherein the ratio between the benzyl ester of the compound of formula (I) and a compound of formula (II) is from about 1:1.2 to about 1:18.8.

8. A method of controlling undesirable vegetation comprising:

contacting a plant, wherein the plant is undesirable vegetation, an area adjacent to the plant, soil, or water, wherein the soil or the water allows for the growth of the undesirable vegetation, with a herbicidally effective amount of a combination comprising (a) a compound of the formula (I):

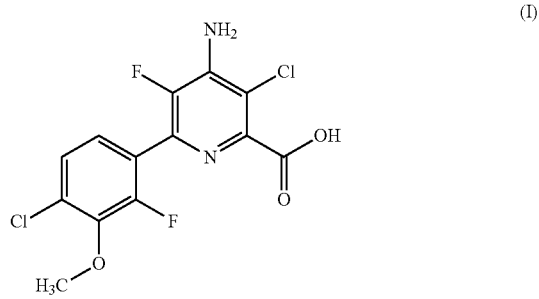 [SMILES: COc1c(Cl)ccc(-c2nc(C(=O)O)c(Cl)c(N)c2F)c1F]

or an alkyl or benzyl ester, or an agriculturally acceptable salt of formula (I) and (b) a compound selected from the group consisting of: azoxystrobin, carbendazim, difenoconazole, flutolanil, hexaconazole, isoprothiolane, isotianil, kasugamycin, mancozeb, myclobutanil, phthalide, probenazole, propiconazole, pyroquilon, tebuconazole, thifluzamide, tricyclazole, trifloxystrobin, and a compound of formula (II):

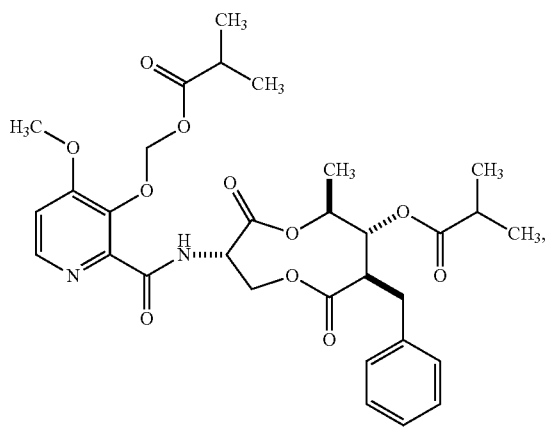

wherein (a) and (b) are present in the combination in a ratio such that the combination exhibits herbicidal synergy; wherein the undesirable vegetation is controlled in at least one of direct-seeded, water-seeded and transplanted rice, cereals, wheat, barley, oats, rye, sorghum, maize, and canola, wherein a weight ratio of the compound of formula (I) or an alkyl or benzyl ester, or an agriculturally acceptable salt of formula (I) to azoxystrobin is from about 1:500 to about 12:1, the weight ratio of the compound of formula (I) or an alkyl or benzyl ester, or an agriculturally acceptable salt of formula (I) to carbendazim is from about 1:375 to about 12:1 the weight ratio of the compound of formula (I) or an alkyl or benzyl ester, or an agriculturally acceptable salt of formula (I) to difenoconazole is from about 1:250 to about 12:1, the weight ratio of the compound of formula (I) or an alkyl or benzyl ester, or an agriculturally acceptable salt of formula (I) to flutolanil is from about 1:500 to about 12:1, the weight ratio of the compound of formula (I) or an alkyl or benzyl ester, or an agriculturally acceptable salt of formula (I) to hexaconazole is from about 1:250 to about 60:1, the weight ratio of the compound of formula (I) or an alkyl or benzyl ester, or an agriculturally acceptable salt of formula (I) to isoprothiolane is from about 1:500 to about 6:1, the weight ratio of the compound of formula (I) or an alkyl or benzyl ester, or an agriculturally acceptable salt of formula (I) to isotianil is from about 1:500 to about 30:1, the weight ratio of the compound of formula (I) or an alkyl or benzyl ester, or an agriculturally acceptable salt of formula (I) to kasugamycin is from about 1:250 to about 150:1, the weight ratio of the compound of formula (I) or an alkyl or benzyl ester, or an agriculturally acceptable salt of formula (I) to mancozeb is from about 1:2500 to about 12:1, the weight ratio of the compound of formula (I) or an alkyl or benzyl ester, or an agriculturally acceptable salt of formula (I) to myclobutanil is from about 1:250 to about 12:1, the weight ratio of the compound of formula (I) or an alkyl or benzyl ester, or an agriculturally acceptable salt of formula (I) to phthalide is from about 1:500 to about 15:1, the weight ratio of the compound of formula (I) or an alkyl or benzyl ester, or an agriculturally acceptable salt of formula (I) to probenazole is from about 1:2500 to about 6:1, the weight ratio of the compound of formula (I) or an alkyl or benzyl ester, or an agriculturally acceptable salt of formula (I) to propiconazole is from about 1:250 to about 30:1, the weight ratio of the compound of formula (I) or an alkyl or benzyl ester, or an agriculturally acceptable salt of formula (I) to pyroquilon is from about 1:1500 to about 3:1, the weight ratio of the compound of formula (I) or an alkyl or benzyl ester, or an agriculturally acceptable salt of formula (I) to tebuconazole is from about 1:250 to about 12:1, the weight ratio of the compound of formula (I) or an alkyl or benzyl ester, or an agriculturally acceptable salt of formula (I) to thifluzamide is from about 1:375 to about 30:1, the weight ratio of the compound of formula (I) or an alkyl or benzyl ester, or an agriculturally acceptable salt of formula (I) to tricyclazole is from about 1:500 to about 15:1, the weight ratio of the compound of formula (I) or an alkyl or benzyl ester, or an agriculturally acceptable salt of formula (I) to trifloxystrobin is from about 1:250 to about 30:1, or the weight ratio of compound of formula (I) or an alkyl or benzyl ester, or an agriculturally acceptable salt of formula (I) to a compound of formula (II) is from about 1:375 to about 150:1.

9. The method of claim 8, wherein the undesirable vegetation is immature.

10. The method of claim 8, wherein the (a) and (b) are applied to water.

11. The method of claim 10, wherein the water is part of a flooded rice paddy.

12. The method of claim 8, wherein the (a) and (b) are applied pre-emergently and/or post emergently to the undesirable vegetation in a crop.

13. The method of claim 8, wherein the (a) and (b) are applied post-emergently to the undesirable vegetation in a crop.

14. The method of claim 8, wherein the undesirable vegetation is controlled in glyphosate-, 5-enolpyruvylshikimate-3-phosphate synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase inhibitor-, imidazolinone-, sulfonylurea-, pyrimidinylthiobenzoate-, triazolopyrimidine-, sulfonylaminocarbonyltriazolinone-, acetolactate synthase or acetohydroxy acid synthase inhibitor-, 4-hydroxyphenyl-pyruvate dioxygenase inhibitor-, phytoene desaturase inhibitor-, carotenoid biosynthesis inhibitor-, protoporphyrinogen oxidase inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant crops.

15. The method of claim 14, wherein the tolerant crops possess multiple or stacked traits conferring tolerance to multiple herbicides.

16. The method of claim 8, wherein the undesirable vegetation comprises a herbicide resistant or tolerant plant.

17. The method of claim 16, wherein the resistant or tolerant plant is resistant or tolerant to multiple herbicides.

18. The method of claim 16, wherein the resistant or tolerant plant is resistant or tolerant to acetolactate synthase or acetohydroxy acid synthase inhibitors, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid synthesis inhibitors, protoporphyrinogen oxidase inhibitors, carotenoid biosynthesis inhibitors, very long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

19. The method of claim 17, wherein the resistant or tolerant plant is a biotype resistant or tolerant to acetolactate synthase or acetohydroxy acid synthase inhibitors, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid synthesis inhibitors, protoporphyrinogen oxidase inhibitors, carotenoid biosynthesis inhibitors, very long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

20. The method of claim 8, wherein (b) is selected from the group consisting of isoprothiolane, phthalide, and pyroquilon.

21. The method of claim 8, wherein the ratio between the compound of the formula (I) and azoxystrobin is from about 1:11.8 to about 1:47.2; the ratio between the benzyl ester of the compound of formula (I) and azoxystrobin is from about 1:1.95 to about 1:57.1; wherein the ratio between the benzyl ester of the compound of formula (I) and carbendazim is from about 1:3.9 to about 1:31.3; wherein the ratio between the compound of the formula (I) and difenoconazole is from about 1:9.4 to about 1:37.7; wherein the ratio between the benzyl ester of the compound of formula (I) and difenoconazole is from about 1:1.6 to about 1:45.7; wherein the ratio between the benzyl ester of the compound of formula (I) and flutolanil is from about 1:8.8 to about 1:70; wherein the ratio between the benzyl ester of the compound of formula (I) and hexaconazole is from about 1.3:1 to about 1:12.5; wherein the ratio between the benzyl ester of the compound of formula (I) and isoprothiolane is from about 1:6.3 to about 1:66.6; wherein the ratio between the benzyl ester of the compound of formula (I) and isotianil is from about 1:3.1 to about 1:47.5; wherein the ratio between the benzyl ester of the compound of formula (I) and kasugamycin is from about 1.8:1 to about 1:8.8; wherein the ratio between the benzyl ester of the compound of formula (I) and mancozeb is from about 1:26.3 to about 1:210; wherein the ratio between the compound of the formula (I) and myclobutanil is from about 1:11.8 to about 1:23.6; wherein the ratio between the benzyl ester of the compound of formula (I) and myclobutanil is from about 1:1.6 to about 1:57.1; wherein the ratio between the benzyl ester of the compound of formula (I) and phthalide is from about 1:6.3 to about 1:37.5; wherein the ratio between the benzyl ester of the compound of formula (I) and probenazole is from about 1:31.3 to about 1:500; wherein the ratio between the compound of the formula (I) and propiconazole is from about 1:9 to about 1:35.9; wherein the ratio between the benzyl ester of the compound of formula (I) and propiconazole is from about 1:4 to about 1:31.3; wherein the ratio between the benzyl ester of the compound of formula (I) and pyroquilon is from about 1:28.9 to about 1:115.6; wherein the ratio between the compound of the formula (I) and tebuconazole is from about 1:11.8 to about 1:47.2; wherein the ratio between the benzyl ester of the compound of formula (I) and tebuconazole is from about 1:2.0 to about 1:57.1; wherein the ratio between the benzyl ester of the compound of formula (I) and thifluzamide is from about 1:2.3 to about 1:9.4; wherein the ratio between the compound of the formula (I) and tricyclazole is from about 1:9.4 to about 1:37.7; wherein the ratio between the benzyl ester of the compound of formula (I) and tricyclazole is from about 1:1.6 to about 1:93.8; wherein the ratio between the benzyl ester of the compound of formula (I) and trifloxystrobin is from about 1:8.8 to about 1:37.5; wherein the ratio between the benzyl ester of the compound of formula (I) and a compound of formula (II) is from about 1:1.2 to about 1:18.8.

* * * * *